United States Patent [19]

Kawakubo et al.

[11] Patent Number: 5,621,103
[45] Date of Patent: Apr. 15, 1997

[54] TETRAHYDROPYRIDINE DERIVATIVE HAVING SUBSTITUENTS ON THREE RINGS

[75] Inventors: Hiromu Kawakubo; Tadashi Nagatani, both of Nobeoka; Showa Ueki, deceased, late of Fukuoka, all of Japan, by Teruko Ueki, legal representative

[73] Assignee: Asahi Kasei Kogyo Kabushiki Kaisha, Osaka, Japan

[21] Appl. No.: 307,779

[22] PCT Filed: Apr. 10, 1992

[86] PCT No.: PCT/JP92/00460

§ 371 Date: Dec. 28, 1994

§ 102(e) Date: Dec. 28, 1994

[87] PCT Pub. No.: WO93/21189

PCT Pub. Date: Oct. 28, 1993

[51] Int. Cl.⁶ .................. C07D 495/04; C07D 471/04; A61K 31/44
[52] U.S. Cl. .............................. 546/80; 514/291
[58] Field of Search ............................... 546/80

[56] References Cited

U.S. PATENT DOCUMENTS 5,104,876 4/1992 Piwinski et al. .................. 514/254

*Primary Examiner*—Alan L. Rotman
*Assistant Examiner*—A. Rotman
*Attorney, Agent, or Firm*—Sughrue, Mion, Zinn, Macpeak & Seas

[57] ABSTRACT

A tetrahydropyridine derivative having substituents on three rings represented by the following formula (1):

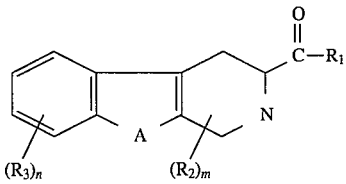

(wherein A represents sulfur atom, sulfoxide group or sulfone group; $R_1$ represents an amino group substituted with a specific substituent or a specific aliphatic oxy group; $R_2$ and $R_3$ each represents hydrogen atom or a hydroxy group; and m and n are each an integer of from 0 to 4; provided that when m and n are 2 or above, $R_2$'s and $R_3$'s may be either the same or different from each other respectively, that when A is sulfur atom and $R_1$ is cyclohexylamino group and $R_2$ is hydrogen atom, $R_3$ is hydroxy group, that when A is sulfoxide group and $R_1$ is cyclohexylamino group or 4-hydroxycyclohexylamino group, $R_2$ is hydrogen atom and $R_3$ is hydrogen atom or hydroxy group and that when A is sulfone group and $R_1$ is cyclohexylamino group, $R_2$ and $R_3$ are each hydrogen atom) and an acid addition salt thereof is to be provided, thereby a compound which is useful as a psychotropic drug having anxiolytic and learning-improvement effects is to be provided.

2 Claims, No Drawings

TETRAHYDROPYRIDINE DERIVATIVE HAVING SUBSTITUENTS ON THREE RINGS

CROSS-REFERENCE

This application is a 371 of PCT/JP 92/00460 filed Apr. 10, 1992.

TECHNICAL FIELD

This invention relates to a tetrahydropyridine derivative having substituents on three rings and represented by the following formula (1), which affects the central nerve of mammal and is useful as a psychotropic drug having antianxiety and learning-improvement effects, and an acid addition salt thereof.

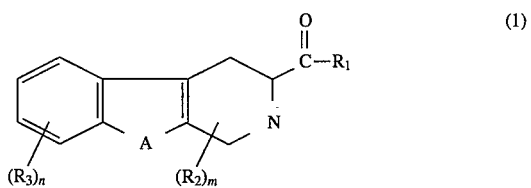

(1)

BACKGROUND ART

There have been known that the following compounds (1), (2), (3), (4), (5), (6) and (7) are useful as an anxiolytic drug and a psychotropic drug.
(1) JP-A-56-43283 (the term "JP-A" as used herein means an "unexamined published Japanese patent application"):

It has been known that a β-carboline-3-carboxylic acid derivative of the following general formula:

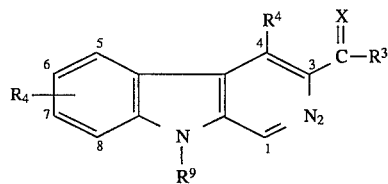

is useful as a neuroleptic having an antiaggresive action.

Also, it has been known that the following tetrahydropyridine derivatives and pyridine derivatives (2), (3), (4), (5), (6) and (7) have psychotropic effects.
(2) JP-A-61-236779:
A compound of the following formula:

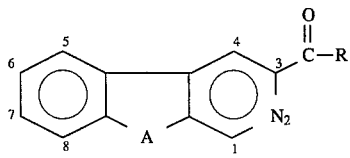

(3) JP-A-63-096188:
A compound of the following formula:

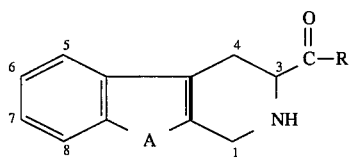

(4) JP-A-63-096189:
A compound of the following formula:

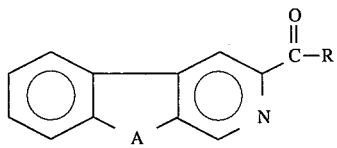

(5) JP-A-1-100172:
A compound of the following formula:

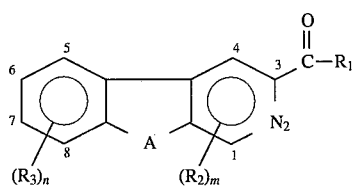

(6) JP-A-2-149583:
A compound of the following formula:

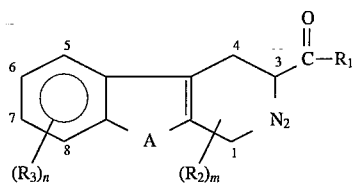

(7) WO89-12447:
A compound of the following formula:

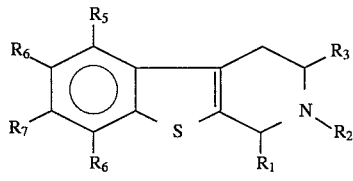

Further, there have been made many studies on the synthesis of 1,2,3,4-tetrahydrobenzo[b]thieno[2,3-c]pyridine or derivatives thereof as reported, for example, in Gerhard Wolf and Felix Zymalkowski, Arch. Pharm., 279, 309 (1976)] and biochemical studies on the effects of these compounds on the brain, as reported, for example, in Bradley V. Clineschmidt, Duane R. Reiss, Douglas J. Pettibone and Janet L. Robinson, J. Pharmacol. Exp. Ther., 696–708, 235 (3) (1985). However no such a tetrahydropyridine derivative having substituents on three rings as the one of the present invention has been known so far.

It is an object of the present invention to provide a novel tetrahydropyridine derivative having substituents on three rings which is useful as a drug having antianxiety and learning-improvement effects.

DISCLOSURE OF THE INVENTION

The present inventors have conducted extensive studies in order to develop such a compound which is a tetrahydropyridine derivative having substituents on three rings and shows antianxiety and learning-improvement effects. As a result, they have successfully found out that a tetrahydropyridine derivative on three rings having a specific substituent at the 3-position suits the purpose. The present invention has been completed based on this finding.

Accordingly, the present invention provides a tetrahydropyridine derivative having substituents on three rings and represented by the following formula:

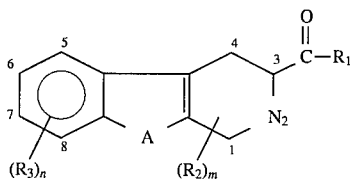

(wherein A represents sulfur atom, sulfoxide group or sulfone group; $R_1$ represents 4-hydroxycyclohexylamino group, 2-hydroxycyclohexylamino group, 4-methylcylcohexylamino group, 2-methylcyclohexylamino group, 4-tert-butylcyclohexylamino group, 4-aminocyclohexylamino group, piperidinoamino group, 1-(4-methylpiperazinyl)amino group, (2,6-dimethylpiperidino)amino group, (1-pyrrolidinyl)amino group, 1-{4-(2-hydroxyethyl)piperazinyl}amino group, 4-(1,2-diethylpyrazolidinyl)amino group, N-cyclohexyl-N-methylamino group, 4-pyridylamino group, phenylamino group, (1-pyrrolinyl)amino group, 4-(1,2,4-triazolyl)amino group, cyclooctylamino group, N-(4-piperidinyl)methylamino group, cyclohexylmethylamino group, 3-pentylamino group, diethylamino group, 1-adamantaneamino group, 3-quinuclidinylamino group, exo-2-norbornaneamino group, 1-(3-chlorophenyl)piperazinyl group, piperonylamino group, 2-methoxybenzylamino group, 3-methoxybenzylamino group, 4-methoxybenzylamino group, 2,3-dimethoxybenzylamino group, 2,4-dimethoxybenzylamino group, 3,4-dimethoxybenzylamino group, 3,5-dimethoxybenzylamino group, 2,4,6-trimethoxybenzylamino group, 3,4,5-trimethoxybenzylamino group, α-methylbenzylamino group, 4-methylbenzylamino group, 4-(trifluoromethyl)benzylamino group, 4-(isopropyl)benzylamino group, 4-(tert-butyl)benzylamino group, 4-isopropylphenylamino group, 4-tert-butylphenylamino group, trans-2-phenylcyclopropylamino group, 1-ethynylcyclohexylamino group, cyclononylamino group, cyclodecanylamino group, 2,3-dimethylcyclohexylamino group, tert-butylamino group, isoamylamino group, (−)-cis-myrtanylamino group, endo-2-norbornaneamino group, cyclododecylamino group, isobutylamino group, diisopropylamino group, 1,3-dimethylbutylamino group, 2-heptylamino group, 4-heptylamino group, 2-octylamino group, sec-butylamino group, 2-pentylamino group, tert-amylamino group, 1,2-dimethylpropylamino group, 1,5-dimethylhexylamino group, 2-ethylhexylamino group, 1,1,3,3-tetramethylbutylamino group, octylamino group, (S)-(−)-2-methylbutylamino group, 3,3-dimethylpropylamino group, cyclohexyloxy group, cyclopentyloxy group, cycloheptyloxy group, cyclooctyloxy group, cyclohexylmethyloxy group or cyclohexylamino group; $R_2$ and $R_3$ each represents hydrogen atom or hydroxy group; and m and n are each an integer of from 0 to 4; provided that when m and n are 2 or above, $R_2$'s and $R_3$'s may be either the same or different from each other respectively, that when A is sulfur atom and $R_1$ is cyclohexylamino group and $R_2$ is hydrogen atom, $R_3$ is hydroxy group, that when A is sulfoxide group and $R_1$ is cyclohexylamino group or 4-hydroxycyclohexylamino group, $R_2$ is hydrogen atom and $R_3$ is hydrogen atom or hydroxy group and that when A is sulfone group and $R_1$ is cyclohexylamino group, $R_2$ and $R_3$ are each hydrogen atom;) and an acid addition salt thereof.

Preferred examples of $R_1$ include 2-hydroxycyclohexylamino group and piperonylamino group.

Examples of the acid addition salt include pharmacologically acceptable ones, e.g., acid addition salts of inorganic acids such as hydrochloric acid, sulfuric acid and phosphoric acid and organic acids such as acetic acid, p-toluenesulfonic acid, methanesulfonic acid, tartaric acid and maleic acid.

Examples of the tetrahydropyridine derivatives having substituents on three rings according to the present invention include the followings.

(1) N-(trans-4-hydroxycyclohexyl)-1,2,3,4-tetrahydrobenzo[b]thieno[2,3-c]pyridine-3-carboxamide
(2) N-(cis-4-hydroxycyclohexyl)-1,2,3,4-tetrahydrobenzo[b]thieno[2,3-c]pyridine-3-carboxamide
(3) (+)-N-(trans-4-hydroxycyclohexyl)-1,2,3,4-tetrahydrobenzo[b]thieno[2,3-c]pyridine-3-carboxamide
(4) (+)-N-(cis-4-hydroxycyclohexyl)-1,2,3,4-tetrahydrobenzo[b]thieno[2,3-c]pyridine-3-carboxamide
(5) (−)-N-(trans-4-hydroxycyclohexyl)-1,2,3,4-tetrahydrobenzo[b]thieno[2,3-c]pyridine-3-carboxamide
(6) (−)-N-(cis-4-hydroxycyclohexyl)-1,2,3,4-tetrahydrobenzo[b]thieno[2,3-c]pyridine-3-carboxamide
(7) N-(2-hydroxycyclohexyl)-1,2,3,4-tetrahydrobenzo[b]thieno[2,3-c]pyridine-3-carboxamide
(8) N-(4-methylcyclohexyl)-1,2,3,4-tetrahydrobenzo[b]thieno[2,3-c]pyridine-3-carboxamide
(9) N-(2-methylcyclohexyl)-1,2,3,4-tetrahydrobenzo[b]thieno[2,3-c]pyridine-3-carboxamide
(10) N-(4-tert-butylcyclohexyl)-1,2,3,4-tetrahydrobenzo[b]thieno[2,3-c]pyridine-3-carboxamide
(11) N-(4-aminocyclohexyl)-1,2,3,4-tetrahydrobenzo[b]thieno[2,3-c]pyridine-3-carboxamide
(12) N-piperidino-1,2,3,4-tetrahydrobenzo[b]thieno[2,3-c]pyridine-3-carboxamide
(13) N-{1-(4-methylpiperazinyl)}-1,2,3,4-tetrahydrobenzo[b]thieno[2,3-c]pyridine-3-carboxamide
(14) N-(2,6-dimethylpiperidino)-1,2,3,4-tetrahydrobenzo[b]thieno[2,3-c]pyridine-3-carboxamide
(15) N-(1-pyrrolidinyl)-1,2,3,4-tetrahydrobenzo[b]thieno[2,3-c]pyridine-3-carboxamide
(16) N-[1-{4-(2-hydroxyethyl)piperazinyl}]-1,2,3,4-tetrahydrobenzo[b]thieno[2,3-c]pyridine-3-carboxamide
(17) N-{4-(1,2-diethylpyrazolidinyl)}-1,2,3,4-tetrahydrobenzo[b]thieno[2,3-c]pyridine-3-carboxamide
(18) N-cyclohexyl-N-methyl-1,2,3,4-tetrahydrobenzo[b]thieno[2,3-c]pyridine-3-carboxamide
(19) N-(4-pyridyl)-1,2,3,4-tetrahydrobenzo[b]thieno[2,3-c]pyridine-3-carboxamide
(20) N-phenyl-1,2,3,4-tetrahydrobenzo[b]thieno[2,3-c]pyridine-3-carboxamide
(21) N-(1-pyrrolinyl)-1,2,3,4-tetrahydrobenzo[b]thieno[2,3-c]pyridine-3-carboxamide
(22) N-{4-(1,2,4-triazolyl)}-1,2,3,4-tetrahydrobenzo[b]thieno[2,3-c]pyridine-3-carboxamide
(23) N-cyclooctyl-1,2,3,4-tetrahydrobenzo[b]thieno[2,3-c]pyridine-3-carboxamide
(24) N-(4-piperidinyl)methyl-1,2,3,4-tetrahydrobenzo[b]thieno[2,3-c]pyridine-3-carboxamide
(25) N-cyclohexylmethyl-1,2,3,4-tetrahydrobenzo[b]thieno[2,3-c]pyridine-3-carboxamide
(26) N-(3-pentyl)-1,2,3,4-tetrahydrobenzo[b]thieno[2,3-c]pyridine-3-carboxamide
(27) N-diethyl-1,2,3,4-tetrahydrobenzo[b]thieno[2,3-c]pyridine-3-carboxamide
(28) N-(1-adamantyl)-1,2,3,4-tetrahydrobenzo[b]thieno[2,3-c]pyridine-3-carboxamide
(29) N-(3-quinuclidinyl)-1,2,3,4-tetrahydrobenzo[2,3-c]pyridine-3-carboxamide
(30) N-(exo-2-norbornyl)-1,2,3,4-tetrahydrobenzo[b]thieno[2,3-c]pyridine-3-carboxamide
(31) 1-(3-chlorophenyl)-4-{3-(1,2,3,4-tetrahydrobenzo[b]thieno[2,3-c]pyridine)carbonyl}piperazine

(32) N-piperonyl-1,2,3,4-tetrahydrobenzo[b]thieno[2,3-c]pyridine-3-carboxamide
(33) N-(2-methoxybenzyl)-1,2,3,4-tetrahydrobenzo[b]thieno[2,3-c]pyridine-3-carboxamide
(34) N-(3-methoxybenzyl)-1,2,3,4-tetrahydrobenzo[b]thieno[2,3-c]pyridine-3-carboxamide
(35) N-(4-methoxybenzyl)-1,2,3,4-tetrahydrobenzo[b]thieno[2,3-c]pyridine-3-carboxamide
(36) N-(2,3-dimethoxybenzyl)-1,2,3,4-tetrahydrobenzo[b]thieno[2,3-c]pyridine-3-carboxamide
(37) N-(2,4-dimethoxybenzyl)-1,2,3,4-tetrahydrobenzo[b]thieno[2,3-c]pyridine-3-carboxamide
(38) N-(3,4-dimethoxybenzyl)-1,2,3,4-tetrahydrobenzo[b]thieno[2,3-c]pyridine-3-carboxamide
(39) N-(3,5-dimethoxybenzyl)-1,2,3,4-tetrahydrobenzo[b]thieno[2,3-c]pyridine-3-carboxamide
(40) N-(2,4,6-trimethoxybenzyl)-1,2,3,4-tetrahydrobenzo[b]thieno[2,3-c]pyridine-3-carboxamide
(41) N-(3,4,5-trimethoxybenzyl)-1,2,3,4-tetrahydrobenzo[b]thieno[2,3-c]pyridine-3-carboxamide
(42) N-(α-methylbenzyl)-1,2,3,4-tetrahydrobenzo[b]thieno[2,3-c]pyridine-3-carboxamide
(43) N-(4-methylbenzyl)-1,2,3,4-tetrahydrobenzo[b]thieno[2,3-c]pyridine-3-carboxamide
(44) N-[4-(trifluoromethyl)benzyl]-1,2,3,4-tetrahydrobenzo[b]thieno[2,3-c]pyridine-3-carboxamide
(45) N-[4-(isopropyl)benzyl]-1,2,3,4-tetrahydrobenzo[b]thieno[2,3-c]pyridine-3-carboxamide
(46) N-[4-(tert-butyl)benzyl]-1,2,3,4-tetrahydrobenzo[b]thieno[2,3-c]pyridine-3-carboxamide
(47) N-[4-(isopropyl)phenyl]-1,2,3,4-tetrahydrobenzo[b]thieno[2,3-c]pyridine-3-carboxamide
(48) N-[4-(tert-butyl)phenyl]-1,2,3,4-tetrahydrobenzo[b]thieno[2,3-c]pyridine-3-carboxamide
(49) N-[trans-2-(phenylcyclopropyl)]-1,2,3,4-tetrahydrobenzo[b]thieno[2,3-c]pyridine-3-carboxamide
(50) N-ethynylcyclohexyl-1,2,3,4-tetrahydrobenzo[b]thieno[2,3-c]pyridine-3-carboxamide
(51) N-cyclononyl-1,2,3,4-tetrahydrobenzo[b]thieno[2,3-c]pyridine-3-carboxamide
(52) N-cyclodecanyl-1,2,3,4-tetrahydrobenzo[b]thieno[2,3-c]pyridine-3-carboxamide
(53) N-(2,3-dimethylcyclohexyl)-1,2,3,4-tetrahydrobenzo[b]thieno[2,3-c]pyridine-3-carboxamide
(54) N-(tert-butyl)-1,2,3,4-tetrahydrobenzo[b]thieno[2,3-c]pyridine-3-carboxamide
(55) N-(isoamyl)-1,2,3,4-tetrahydrobenzo[b]thieno[2,3-c]pyridine-3-carboxamide
(56) N-[(−)-cis-myrtanyl]-1,2,3,4-tetrahydrobenzo[b]thieno[2,3-c]pyridine-3-carboxamide
(57) N-(endo-2-norbornyl)-1,2,3,4-tetrahydrobenzo[b]thieno[2,3-c]pyridine-3-carboxamide
(58) N-cyclododecyl-1,2,3,4-tetrahydrobenzo[b]thieno[2,3-c]pyridine-3-carboxamide
(59) N-(isobutyl)-1,2,3,4-tetrahydrobenzo[b]thieno[2,3-c]pyridine-3-carboxamide
(60) N-diisopropyl-1,2,3,4-tetrahydrobenzo[b]thieno[2,3-c]pyridine-3-carboxamide
(61) N-(1,3-dimethylbutyl)-1,2,3,4-tetrahydrobenzo[b]thieno[2,3-c]pyridine-3-carboxamide
(62) N-(2-heptyl)-1,2,3,4-tetrahydrobenzo[b]thieno[2,3-c]pyridine-3-carboxamide
(63) N-(4-heptyl)-1,2,3,4-tetrahydrobenzo[b]thieno[2,3-c]pyridine-3-carboxamide
(64) N-(2-octyl)-1,2,3,4-tetrahydrobenzo[b]thieno[2,3-c]pyridine-3-carboxamide
(65) N-(sec-butyl)-1,2,3,4-tetrahydrobenzo[b]thieno[2,3-c]pyridine-3-carboxamide
(66) N-(2-pentyl)-1,2,3,4-tetrahydrobenzo[b]thieno[2,3-c]pyridine-3-carboxamide
(67) N-(tert-amyl)-1,2,3,4-tetrahydrobenzo[b]thieno[2,3-c]pyridine-3-carboxamide
(68) N-(1,2-dimethylpropyl)-1,2,3,4-tetrahydrobenzo[b]thieno[2,3-c]pyridine-3-carboxamide
(69) N-(1,5-dimethylhexyl)-1,2,3,4-tetrahydrobenzo[b]thieno[2,3-c]pyridine-3-carboxamide
(70) N-(2-ethylhexyl)-1,2,3,4-tetrahydrobenzo[b]thieno[2,3-c]pyridine-3-carboxamide
(71) N-(1,1,3,3-tetramethylbutyl)-1,2,3,4-tetrahydrobenzo[b]thieno[2,3-c]pyridine-3-carboxamide
(72) N-octyl-1,2,3,4-tetrahydrobenzo[b]thieno[2,3-c]pyridine-3-carboxamide
(73) N-[(S)-(−)-2-methylbutyl]-1,2,3,4-tetrahydrobenzo[b]thieno[2,3-c]pyridine-3-carboxamide
(74) N-(3,3-dimethylpropyl)-1,2,3,4-tetrahydrobenzo[b]thieno[2,3-c]pyridine-3-carboxamide
(75) cyclohexyl 1,2,3,4-tetrahydrobenzo[b]thieno[2,3-c]pyridine-3-carboxylate
(76) cyclopentyl 1,2,3,4-tetrahydrobenzo[b]thieno[2,3-c]pyridine-3-carboxylate
(77) cycloheptyl 1,2,3,4-tetrahydrobenzo[b]thieno[2,3-c]pyridine-3-carboxylate
(78) cyclooctyl 1,2,3,4-tetrahydrobenzo[b]thieno[2,3-c]pyridine-3-carboxylate
(79) cyclohexylmethyl 1,2,3,4-tetrahydrobenzo[b]thieno[2,3-c]pyridine-3-carboxylate
(80) N-cyclohexyl-6-hydroxy-1,2,3,4-tetrahydrobenzo[b]thieno[2,3-c]pyridine-3-carboxamide
(81) N-cyclohexyl-1,2,3,4-tetrahydrobenzo[b]thieno[2,3-c]pyridine-3-carboxamide-9-oxide
(82) N-cyclohexyl-6-hydroxy-1,2,3,4-tetrahydrobenzo[b]thieno[2,3-c]pyridine-3-carboxamide-9-oxide
(83) N-(4-hydroxycyclohexyl)-6-hydroxy-1,2,3,4-tetrahydrobenzo[b]thieno[2,3-c]pyridine-3-carboxamide-9-oxide
(84) N-cyclohexyl-1,2,3,4-tetrahydrobenzo[b]thieno[2,3-c]pyridine-3-carboxamide-9-dioxide Among the specific examples as cited above, the compounds (7) and (32) are particularly preferable ones.

The compounds of the present invention represented by the above formula (1) can be obtained by the following (Synthesis method 1), (Synthesis method 2) and (Synthesis method 3).

In these reaction schemes, $R_1$, $R_2$ and $R_3$ are each as defined above and R' represents a lower alkyl group having up to 6 carbon atoms. $X_1$ in $HX_1$, $X_2$ in Boc-$X_2$ and $X_3$ in $HX_3$ represent each an atom or group which binds to a hydrogen atom to form thereby an acid such as a halogen atom and methanesulfonic acid or an excellent eliminating group such as a 4,6-dimethylpyrimidinylmercapto group.

(Synthesis method 1)

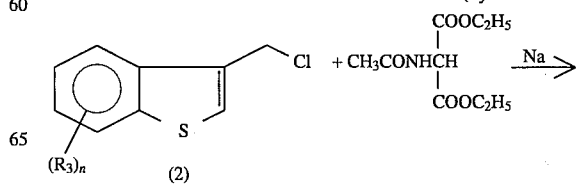

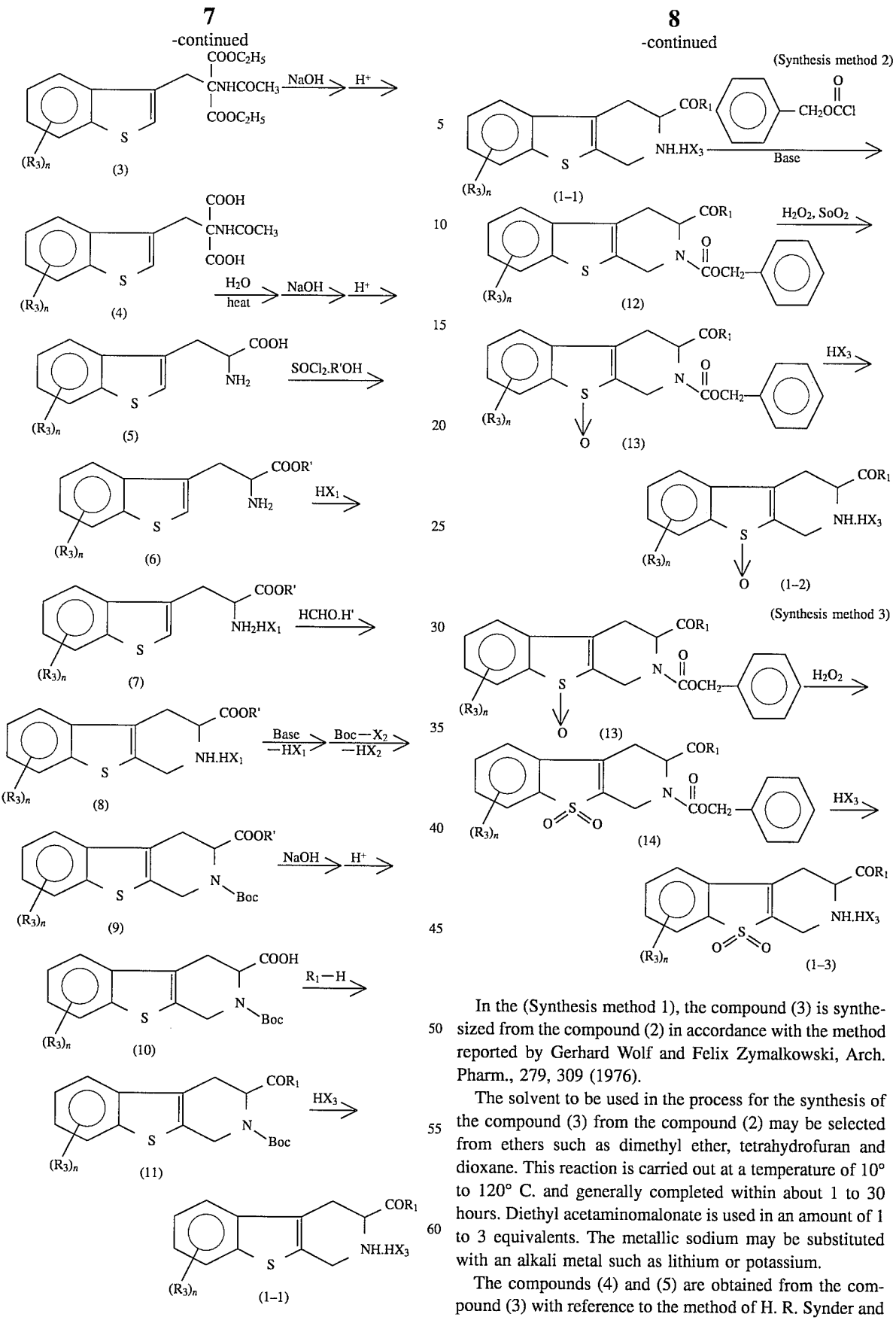

In the (Synthesis method 1), the compound (3) is synthesized from the compound (2) in accordance with the method reported by Gerhard Wolf and Felix Zymalkowski, Arch. Pharm., 279, 309 (1976).

The solvent to be used in the process for the synthesis of the compound (3) from the compound (2) may be selected from ethers such as dimethyl ether, tetrahydrofuran and dioxane. This reaction is carried out at a temperature of 10° to 120° C. and generally completed within about 1 to 30 hours. Diethyl acetaminomalonate is used in an amount of 1 to 3 equivalents. The metallic sodium may be substituted with an alkali metal such as lithium or potassium.

The compounds (4) and (5) are obtained from the compound (3) with reference to the method of H. R. Synder and Curtis W. Smith, "J. Am. Chem. Soc., 66, 350 (1944)".

The solvent to be used in the ester hydrolysis for preparing the compound (4) from the compound (3) may be selected from water or a solvent mixture comprising water with a lower alcohol such as methanol, ethanol or propanol. Further, sodium hydroxide, potassium hydroxide or sodium carbonate is used therein. This reaction is carried out at a temperature of 10° to 100° C. and generally completed within about 1 to 10 hours. As the acid for neutralizing the alkali, citric acid or acetic acid may be used.

The solvent to be used in the decarboxylation and amide hydrolysis for preparing the compound (5) from the compound (4) is water. The decarboxylation is carried out at a temperature of 60° to 100° C. and generally completed within about 1 to 30 hours. In the amide hydrolysis, the sodium hydroxide may be substituted with potassium hydroxide. This reaction is carried out at a temperature of 10° to 100° C. and generally completed within about 1 to 30 hours.

The compound (6) is prepared from the compound (5) with reference to the method reported by Nobuo Izumiya, Tetsuo Kato, Motonori Ono and Tohiko Aoyagi, "Gosei Kagaku Sirizu, Peputido Gosei" (Maruzen) 66, Example 3.2. The alcohol (R'OH) to be used in this method may be selected from among lower alcohols such as methyl alcohol, ethyl alcohol, propyl alcohol and hexyl alcohol. This alcohol serves as a solvent too. As an acid catalyst, thionyl chloride, sulfuric acid, hydrochloric acid gas, p-toluenesulfonic acid etc. may be used. This reaction is carried out at a temperature of 10° to 100° C., preferably 20° to 30° C., and generally completed within about 1 to 48 hours.

The solvent to be used in the process for preparing the compound (7) form the compound (6) may be selected from lower alcohols such as methyl alcohol, ethyl alcohol, propyl alcohol and hexyl alcohol and ethyl acetate. As $HX_1$, sulfuric acid, hydrochloric acid, p-toluenesulfonic acid etc. may be used to give thereby an acid addition salt. This reaction is carried out at a temperature of −10° to 30° C., preferably 0° to 10° C., and completed generally within 1 day.

The compound (8) is synthesized from the compound (7) with reference to the method of D. Soerens et al., J. Org. Chem., 44 (4), 535–545 (1979). Formalin is used usually in an amount of 1 to 10 equivalents, preferably 1.5 to 2 equivalents, based on the compound (7). As the solvent to be used in this process, a solvent mixture of water with a lower alcohol such as methanol, ethanol, propyl alcohol or hexyl alcohol is preferable. This reaction is carried out at a temperature of 10° to 100° C., preferably 50° to 70° C., and generally completed within 1 to 30 hours, preferably 20 to 25 hours. As a reaction catalyst, 10 to 100 equivalents of an acid such as hydrochloric acid, sulfuric acid or p-toluene sulfonic acid is employed.

The compound (9) is prepared from the compound (8) with reference to the method of T. Nakagawa, K. Kuroiwa, K. Narita and Y. Isowa, Bull. Chem Soc. Japan, 1269, 46 (1973).

The solvent to be used in the process of synthesizing the compound (9) from the compound (8) is an organic solvent such as chloroform, methylene chloride, tetrahydrofuran and dimethylformamide. This reaction is carried out at a temperature of 0° to 100° C. and generally completed within 1 to 48 hours. To neutralize $HX_1$ of the compound (8), a tertiary amine such as triethylamine or N-methylmorpholine is used. This tertiary amine is employed in an amount of 2 to 3 equivalents. In order to introduce a tert-butoxycarbonyl group (Boc group), a butoxycarbonylating agent such as Boc-azide may be used. $X_2$ is, for example, thio-4,6-dimethylpyrimidine. Alternately, the Boc group may be substituted with a protecting group for the amino group such as a benzyloxycarbonyl group.

The compound (10) is prepared from the compound (9) with reference to the method of E. Brand, B. F. Erlanger, H. Sacks and J. Polanthick, J. Am. Chem. Soc., 73, 3510 (1951).

In the process for synthesizing the compound (10) form the compound (9), hydrolysis with sodium hydroxide is effected and then followed by the neutralization with an acid. In this reaction, an alcohol such as methanol or ethanol or water is used as a solvent. This reaction is carried out at a temperature of 0° to 80° C. and generally completed within 1 to 48 hours. Sodium hydroxide is used in an amount of from 1 to 3 equivalents. Alternately, the sodium hydroxide is substituted by potassium hydroxide. As the acid for neutralizing the alkali, citric acid or acetic acid is used.

The solvent to be used in the process for preparing the compound (11) from the compound (10) is an aprotic polar solvent such as dimethylformamide or dimethylsulfoxide. As a condensing agent, 1,3-dicyclohexylcarbodiimide (DCC), diphenylphosphoric azide (DPPA) etc. may be used. This reaction is carried out at a temperature of 10° to 100° C., preferably 20° to 30° C. and generally completed within 1 to 10 hours.

The solvent to be used in the process for preparing an acid addition salt of a tetrahydropyridine derivative having substituents on three rings (1-1) from the compound (11) is ethyl acetate or an alcoholic organic solvent such as methyl alcohol or ethyl alcohol. As $HX_3$, sulfuric acid, hydrochloric acid, p-toluenesulfonic acid etc. may be used. This reaction is carried out at a temperature of 10° to 100° C., preferably 40° to 60° C., and generally completed within 1 to 10 hours. The tetrahydropyridine derivative having substituents on three rings (1-1) can be obtained by neutralizing with a base such as sodium hydroxide, potassium hydroxide or triethylamine.

The solvent to be used in the preparation of the compound (12) from the compound (1-1) in the (Synthesis method 2) is an organic solvent such as chloroform, dioxane or ethanol. Chloroform is preferable among all. This reaction is carried out at a temperature of 0° to 150° C., preferably 20° to 60° C. Benzyloxycarbonyl chloride is usually employed in an amount of 1 to 3 equivalents. This reaction is generally completed within 1 to 24 hours. In order to neutralize $HX_3$ and HCl, a tertiary amine such as triethylamine, N-methylmorpholine or 1,8-diazabicyclo[5,4,0]-7-undecene is used.

The solvent to be used in the process for preparing the compound (13) from the compound (12) is an acidic solvent such as acetic acid or hydrochloric acid. This reaction is carried out at a temperature of 10° to 50° C., preferably 10° to 30° C. It is still preferable to use selenium dioxide as a reaction inhibitor for the sulfone group. Hydrogen peroxide is usually employed in an amount of 1 to 2 equivalents, preferably 1 to 1.5 equivalents.

The solvent to be used in the process for preparing the compound (1-2) from the compound (13) is an acidic solvent such as methanesulfonic acid or hydrochloric acid. This reaction is carried out at a temperature of 10° to 50° C., preferably 10° to 30° C.

The solvent to be used in the process for preparing the compound (14) from the compound (13) in the (Synthesis method 3) is an acidic solvent such as acetic acid or hydrochloric acid. This reaction is carried out at a temperature of 10° to 50° C., preferably 10° to 30° C. Hydrogen peroxide is usually employed in an amount of 1 to 2 equivalents, preferably 1 to 1.5 equivalents.

The solvent to be used in the process for preparing the compound (1-3) from the compound (14) is an acidic solvent such as acetic acid, hydrobromic acid, methanesulfonic acid or hydrochloric acid. This reaction is carried out at a temperature of 10° to 50° C., preferably 10° to 30° C.

When the compound represented by the general formula (1) or an acid addition salt thereof is to be used as a psychotropic drug, it is administered either alone or together with pharmaceutically acceptable carriers. The composition is determined depending on, for example, the administration route and the administration schedule.

The dose is determined depending on, for example, the age and weight of the patient, the severity of the disease, the kinds of simultaneous treatments, if any, the frequency of the treatment and the desired effect.

In general, the dose ranges from 0.01 to 20 mg/kg per day (in the case of parenteral administration) or from 0.02 to 40 mg/kg per day (in the case of oral administration).

When the compound represented by formula (1) is to be orally administered, it is used in the form of, for example, tablets, capsules, dusts, granules, solutions or elixirs. In the case of parenteral administration, it is used in the form of a sterilized liquid. When this compound is to be used in the form of the above-mentioned preparations, solid or liquid nontoxic pharmaceutical carriers may be contained in the composition.

As a common example of a solid carrier, gelatin capsules may be cited. Further, the active ingredient is formulated into tablets, granules or dusts, optionally together with auxiliary agents, and packaged. Examples of a filler in these cases include water; gelatin; saccharides such as lactose and glucose; starches such as corn, wheat, rice and maze starches; fatty acids such as stearic acid; fatty acid salts such as calcium stearate and magnesium stearate; talc; vegetable oils; alcohols such as stearyl alcohol and benzyl alcohol; gum; and polyalkylene glycols.

These capsules, tablets, granules and dusts generally contain from 1 to 80% by weight, preferably from 1 to 60% by weight, of the active ingredient.

Preferred examples of liquid carriers include water, physiological saline, solutions of saccharides such as dextrose or the like and glycols such as ethylene glycol, propylene glycol and polyethylene glycol.

When the compound represented by formula (1) is to be parenterally administered through intramuscular, intravenous or subcutaneous injection, it is formulated into an aseptic solution to which another solute such as sodium chloride or glucose is added for the purpose of isotonization.

Examples of solvents suitable for injections include sterilized water, a lidocaine hydrochloride solution (for intramuscular injection), physiological saline, glucose, a liquor for intravenous injection and an electrolyte solution (for intravenous injection). These injections may contain usually from 0.01 to 20% by weight, preferably from 0.01 to 10% by weight, of the active ingredient.

As a liquid preparation for oral administration, a suspension or a syrup containing 0.01 to 20% by weight of the active ingredient is preferred. In such a case, perfumes and water soluble fillers such as a syrup and a pharmaceutical micelle may be used.

BEST MODE FOR CARRYING OUT THE INVENTION

The present invention is explained below in further detail with reference to Examples, but the present invention is not limited thereby.

EXAMPLE 1

First, the synthesis of ethyl 2-amino-(benzo[b]thiophen-3-yl)-propionate hydrochloride will be described.

The following reactions were carried out with reference to H. R. Snyder & Curtis W. Smith, J. Am. Chem. Soc., 66, 350 (1944).

The starting material, 3-chloromethylbenzo[b]thiophene, was synthesized in accordance with the method of Gerhard Wolf & Felix Zymalkowski, Arch. Pharm., 279, 309 (1976).

5.30 g of metallic sodium was cut into small pieces and added to 700 ml of dry dioxane. Further, 50 g of diethyl acetaminomalonate was added thereto at room temperature. After stirring under reflux for a day, 32.3 g of 3-chloromethylbenzo[b]thiophene was added and the mixture was stirred under reflux for 1.5 day. Then the reaction mixture was filtered and the filtrate was concentrated under reduced pressure. The concentrate was separated and purified with a silica gel column to give thereby 30.5 g of a product. The NMR and IR data of this product were as follows. It was confirmed that this product is ethyl-α-acetamino-α-carbethoxy-β-(3-benzo[b]thiophene)propionate (yield: 47%).

IR ($v_{max}$, cm$^{-1}$): 3275, 1740, 1640, 1510

NMR (δ, CDCl$_3$): 1.30 (t, J=6 Hz, 6H), 1.95 (s, 3H), 3.67 (s, 2H), 4.17 (q, J=6 Hz, 4H), 6.50–8.00 (m, 5H)

30.5 g of ethyl-α-acetamino-α-carbethoxy-β-(3-benzo[b]thiophene)propionate was added to 250 ml of methanol. To the obtained methanol solution was added a solution of 13.45 g of sodium hydroxide dissolved in 500 ml of water. After stirring under reflux for 2 hours, the methanol was distilled off under reduced pressure. The aqueous layer was extracted with 300 ml of chloroform twice. The chloroform layer was dried over magnesium sulfate and distilled under reduced pressure to give thereby 16.75 g of a product. The NMR and IR data of this product were as follows. It was confirmed that this product is α-acetamino-α-carboxy-β-(3-benzo[b]thiophene)propionic acid (yield: 65%).

IR ($v_{max}$, cm$^{-1}$): 1730, 1635, 1540

NMR (δ, CDCl$_3$): 1.87 (s, 3H), 3.45 (s, 2H), 7.17–8.00 (m, 5H), 9.33 (s, 2H)

30 g of α-acetamino-α-carboxy-β-(3-benzo[b]thiophene)propionic acid was added to 200 ml of water and stirred under reflux for 3 hours. After returning the reaction temperature to room temperature, 15.6 g of sodium hydroxide was gradually added in thereto. Then the mixture was stirred under reflux for 2.5 days. After the completion of the reaction, the temperature was returned to room temperature and the mixture was washed with 100 ml of chloroform. The aqueous layer was adjusted to pH 4.0 with conc. hydrochloric acid. After allowing to stand in a refrigerator overnight, it was filtered to give thereby 16.0 g of a product. The NMR and IR data of this product were as follows. It was confirmed that this product is 2-amino-(benzo[b]thiophen-3-yl)propionic acid (yield: 74%).

IR ($v_{max}$, cm$^{-1}$): 1590, 1420, 1020

NMR (δ, D$_2$O, (CH$_3$)$_3$Si(CH$_2$)$_3$SO$_3$Na): 3.00–4.00 (m, 3H), 7.20–8.00 (m, 5H)

The following reactions were carried out with reference to Nobuo Izumiya, Tetsuo Kato, Motonori Ono and Tohiko Aoyagi, "Gosei Kagaku Sirizu, Peputido Gosei" (Maruzen) 66, Example 3.2.

920 ml of dry ethanol was cooled to 0° C. and 20.8 ml of thionyl chloride was gradually added thereto. After stirring at 0° C. for 30 minutes, 16.0 g of 2-amino(benzo[b]thiophen-3-yl)propionic acid was added thereto at 0° C., followed by stirring for 30 minutes. Then the mixture was stirred at room temperature for 2 days and the ethanol was distilled off under reduced pressure.

To the residue were added 300 ml of methylene chloride and 150 ml of a 5% aqueous solution of sodium hydrogencarbonate to extract it. The methylene chloride layer was dried over magnesium sulfate and distilled off under reduced pressure to give thereby 16.9 g of a product. The NMR and IR data of this product were as follows. It was confirmed that this product is ethyl 2-amino-(benzo[b]thiophen-3-yl)propionate (yield: 94%).

IR ($v_{max}$, cm$^{-1}$): 3060, 2950, 1760, 1590

NMR (δ, CDCl$_3$): 1.44 (t, J=5 Hz, 3H), 3.0–3.36 (m, 3H), 4.45 (q, J=5 Hz, 2H), 7.18–8.01 (m, 5H)

16.9 g of ethyl 2-amino-(benzo[b]thiophen-3-yl)propionate was dissolved in 50 ml of ethyl acetate. To the resulting solution was added 13.6 ml of 5 N-hydrochloric acid/ethyl acetate. After allowing to stand at room temperature for 12 hours, the crystals thus precipitated were collected by filtration to give thereby 18.8 g of a product. The NMR and IR data of this product were as follows. It was confirmed that this product is ethyl 2-amino-(benzo[b]thiophen-3-yl)propionate hydrochloride (yield: 97%).

IR ($v_{max}$, cm$^{-1}$): 3070, 2950, 2810, 1760, 1595

NMR (δ, D$_2$O, (CD$_3$)$_2$S=O): 1.45 (t, J=5 Hz, 3H), 3.01–3.40 (m, 3H), 4.47 (q, J=5 Hz, 2H), 7.11–8.00 (m, 5H)

N-(trans-4-hydroxycyclohexyl)-1,2,3,4-tetrahydrobenzo[b]thieno[2,3-c]pyridine-3-carboxamide hydrochloride was obtained in the following manner.

23.24 g of ethyl 2-amino-(benzo[b]thiophen-3-yl)propionate hydrochloride and 10.2 ml of formalin were dissolved in a mixture of 200 ml of ethanol with 200 ml of water and stirred under reflux for 3 hours. Then the reaction mixture was approximately halved by concentration and adjusted to pH 9 to 10 with sodium hydrogencarbonate. Then it was extracted with 300 ml of chloroform thrice. The chloroform layer was washed twice with 100 ml of a saturated aqueous solution of sodium chloride and dried over magnesium sulfate. After distilling off the chloroform under reduced pressure, the residue was recrystallized from 100 ml of chloroform/ether (1:1) to give thereby 14.84 g of a product. The NMR and IR data of this product were as follows. It was confirmed that this product is ethyl 1,2,3,4-tetrahydrobenzo[b]thieno[2,3-c]pyridine-3-carboxylate (yield: 69% ).

IR ($v_{max}$, cm$^{-1}$): 2970, 2900, 1720, 1430, 1195, 760, 740

NMR (δ, CDCl$_3$): 1.35 (t, J=6 Hz, 3H), 2.25 (s, 2H), 3.10 (dd, 2H), 3.70–4.00 (m, 1H), 4.30 (q, 2H), 7.30–8.00 (m, 4H)

6 g of ethyl 1,2,3,4-tetrahydrobenzo[b]thieno[2,3-c]pyridine-3-carboxylate and 6.63 g of 2-(2-tert-butoxycarbonylthio)-4,6-dimethylpyrimidine were dissolved in 20 ml of dry chloroform and refluxed for 30 minutes. After distilling off the chloroform under reduced pressure, the residue was dissolved in 300 ml of ethyl acetate, washed successively with 50 ml of a 5% aqueous solution of sodium hydrogencarbonate thrice, a 5% aqueous solution of citric acid twice and a saturated aqueous solution of sodium chloride twice and then dried over sodium sulfate. After distilling off the ethyl acetate under reduced pressure, the residue was recrystallized from chloroform/petroleum ether to give thereby 6.18 g of a product. The NMR and IR data of this product were as follows. It was confirmed that this product is ethyl 2-tert-butoxycarbonyl-1,2,3,4-tetrahydrobenzo[b]thieno[2,3-c]pyridinecarboxylate (yield: 76%).

IR ($v_{max}$, cm$^{-1}$): 2970, 1720, 1695, 1400, 760, 740

NMR (δ, CDCl$_3$): 1.10 (t, J=6 Hz, 3H), 1.50 (s, 9H), 3.40 (m, 2H), 4.05 (q, J=6 Hz, 2H), 4.70 (d, J=9 Hz, 2H), 5.10–5.50 (m, 1H), 7.10–7.70 (m, 4H)

6 g of ethyl 2-tert-butoxycarbonyl-1,2,3,4-tetrahydrobenzo[b]thieno[2,3-c]pyridinecarboxylate was dissolved in a mixture of 30 ml of methanol with 20 ml of chloroform. After adding 4 ml of a 5N aqueous solution of sodium hydroxide, the mixture was refluxed for 5 hours. After distilling off the solvent under reduced pressure, 300 ml of 5% citric acid and 300 ml of chloroform were added thereto. The chloroform layer was washed with a saturated aqueous solution of sodium chloride and dried over sodium sulfate. The chloroform layer was distilled off under reduced pressure and the residue was recrystallized from chloroform-hexane to give thereby 4.15 g of a product. The NMR and IR data of this product were as follows. It was confirmed that this product is 2-tert-butoxycarbonyl-1,2,3,4-tetrahydrobenzo[b]thieno[2,3-c]pyridinecarboxylic acid (yield: 75%).

IR ($v_{max}$, cm$^{-1}$): 2970, 2860, 1700, 1695, 1400, 760, 740

NMR (δ, CDCl$_3$): 1.50 (s, 9H), 3.40 (s, 2H), 4.60 (d, J=9 Hz, 2H), 5.10–5.50 (m, 1H), 7.10–7.70 (m, 4H)

2.0 g of 2-tert-butoxycarbonyl-1,2,3,4-tetrahydrobenzo[b]thieno[2,3-c]pyridinecarboxylic acid was dissolved in 12 ml of dry dimethylformamide. Further, 0.99 g of trans-4-hydroxycyclohexylamine hydrochloride and 0.92 ml of triethylamine were added thereto at 0° C. and the resulting mixture was stirred for 30 minutes. Furthermore, a solution of 1.98 g of diphenyl-phosphoryl azide/10 ml of dry dimethylformamide and 0.92 ml of triethylamine were added thereto and stirred at room temperature for 1 day. The reaction mixture was dissolved in 500 ml of ethyl acetate, successively washed with 25 ml of a 5% aqueous solution of citric acid twice and 25 ml of a saturated aqueous solution of sodium chloride twice and dried over sodium sulfate. After distilling off the ethyl acetate under reduced pressure, the residue was subjected to thin layer column chromatography (developing solvent: chloroform/methanol=9/1). As a result, 2.30 g of a compound of a single spot was obtained. 2.30 g of this product was dissolved in 15 ml of 1 N-hydrochloric acid/ethanol and stirred at room temperature for 2 days. The white crystals thus precipitated were collected by filtration to give thereby 1 g of N-(trans-4-hydroxycyclohexyl)-1,2,3,4-tetrahydrobenzo[b]thieno[2,3-c]pyridine-3-carboxamide hydrochloride (yield: 46%). The NMR and IR data of this product were as follows. It was confirmed that this product is N-(trans-4-hydroxycyclohexyl)-1,2,3,4-tetrahydrobenzo[b]thieno[2,3-c]pyridine-3-carboxamide hydrochloride.

IR ($v_{max}$, cm$^{-1}$): 3310, 2940, 2580, 1665, 1580, 760

NMR (δ, d$_4$-DMSO): 0.77–2.14 (m, 10H), 2.86–4.71 (m, 5H), 7.10–7.95 (m, 4H)

Mass (m/z): 331, 314, 188.

EXAMPLE 2

The procedure of the above Example 1 was repeated except for using 220.99 g of cis-4-hydroxycyclohexylamine hydrochloride in place of 0.99 g of the trans-4-hydroxycyclohexylamine hydrochloride employed in Example 1. Thus N-(cis-4-hydroxycyclohexyl)-1,2,3,4-tetrahydrobenzo[b]thieno[2,3-c]pyridine-3-carboxamide hydrochloride was synthesized. Table 1 shows the result while Table 2 shows the analytical data thereof.

TABLE 1

| 2-Tert-butoxy-carbonyl-1,2,3,4-tetrahydrobenzo[b]-thieno[2,3-c]-pyridinecarboxylic acid | Reactant | Reaction temperature | Reaction time | Final yield | Final product |
|---|---|---|---|---|---|
| 2.0 g | cis-4-hydroxy-cyclohexylamine hydrochloride 0.99 g | room temp. | 1 day | 1.20 g (55%) | N-(cis-4-hydroxycyclohexyl)-1,2,3,4-tetrahydrobenzo[b]thieno-[2,3-c]pyridine-3-carboxamide hydrochloride |

TABLE 2

| IR ($v_{max}$, cm$^{-1}$) | NMR ($\delta$, CD$_3$OD) | Mass (m/z) |
|---|---|---|
| 3350, 2950, 1660, 1548, 1430, 755 | 1.00–2.12(m, 10H), 2.90–4.21 (m, 5H), 6.89–7.97(m, 4H) | 331, 314, 188 |

EXAMPLE 3

(+)-N-(trans-4-hydroxycyclohexyl)-1,2,3,4-tetrahydrobenzo[b]thieno[2,3-c]pyridine-3-carboxamide hydrochloride, (+)-N-(cis-4-hydroxycyclohexyl)-1,2,3,4-tetrahydrobenzo [b]thieno[2,3-c]pyridine-3-carboxamide hydrochloride, (−)-N-(trans-4-hydroxycyclohexyl)-1,2,3,4-tetrahydrobenzo [b]thieno[2,3-c]pyridine-3-carboxamide hydrochloride and (−)-N-(cis-4-hydroxycyclohexyl)-1,2,3,4-tetrahydrobenzo[b]thieno[2,3-c]pyridine-3-carboxamide hydrochloride were synthesized by repeating the procedures of the above Examples 1 and 2 except for using 16.0 g of (+) and (−)-2-amino-(benzo[b]thiophen-3-yl)propionic acid described in Japanese Patent Application No. Hei-2-1222 in place of 16.0 g of the 2-amino-(benzo[b]thiophen-3-yl)-propionic acid employed in Examples 1 and 2. Table 3 shows the results, while Table 4 shows the analytical data.

TABLE 3

| Final compound | 2-Amino-(benzo[b]thiophen-3-yl)propionic acid | Final yield |
|---|---|---|
| (+)-N-(trans-4-hydroxy-cyclohexyl)-1,2,3,4-tetrahydrobenzo[b]thieno-[2,3-c]pyridine-3-carboxamide hydrochloride | (+) form 16 g | 55% |
| (+)-N-(cis-4-hydroxy-cyclohexyl)-1,2,3,4-tetrahydrobenzo[b]thieno-[2,3-c]pyridine-3-carboxamide hydrochloride | (+) form 16 g | 51% |
| (−)-N-(trans-4-hydroxy-cyclohexyl)-1,2,3,4-tetrahydrobenzo[b]thieno-[2,3-c]pyridine-3-carboxamide hydrochloride | (−) form 16 g | 49% |
| (−)-N-(cis-4-hydroxy-cyclohexyl)-1,2,3,4-tetrahydrobenzo[b]thieno-[2,3-c]pyridine-3-carboxamide hydrochloride | (−) form 16 g | 50% |

TABLE 4

| Final compound | IR ($v_{max}$, cm$^{-1}$) | NMR ($\delta$, CD$_3$OD) | Mass (m/z) |
|---|---|---|---|
| (+)-N-(trans-4-hydroxy-cyclohexyl)-1,2,3,4-tetrahydrobenzo[b]thieno-[2,3-c]pyridine-3-carboxamide hydrochloride | 3345, 2935, 1660, 1550, 1425, 755 | 0.98–2.22 (m, 10H), 2.94–4.18 (m, 5H), 6.78–7.95 (m, 4H) | 331, 314, 188 |
| (+)-N-(cis-4-hydroxy-cyclohexyl)-1,2,3,4-tetrahydrobenzo[b]thieno-[2,3-c]pyridine-3-carboxamide hydrochloride | 3340, 2940, 1660, 1545, 1430, 755 | 1.11–2.12 (m, 10H), 2.96–4.22 (m, 5H), 6.75–7.91 (m, 4H) | 331, 314, 188 |
| (−)-N-(trans-4-hydroxy-cyclohexyl)-1,2,3,4-tetrahydrobenzo[b]thieno-[2,3-c]pyridine-3-carboxamide hydrochloride | 3345, 2935, 1660, 1550, 1425, 755 | 0.98–2.22 (m, 10H), 2.94–4.18 (m, 5H), 6.78–7.95 (m, 4H) | 331, 314, 188 |
| (−)-N-(cis-4-hydroxy-cyclohexyl)-1,2,3,4-tetrahydrobenzo[b]thieno-[2,3-c]pyridine-3-carboxamide hydrochloride | 3340, 2940, 1660, 1545, 1430, 755 | 1.11–2.12 (m, 10H), 2.96–4.22 (m, 5H), 6.75–7.91 (m, 4H) | 331, 314, 188 |

EXAMPLE 4

The procedure of the above Example 1 was repeated except for replacing 0.99 g of the trans-4-hydroxycyclohexylamine hydrochloride employed in Example 1 with the equivalent amount of each of the corresponding amino compounds to synthesize thereby N-(2-hydroxycyclohexyl)-1,2,3,4-tetrahydrobenzo[b]thieno[2,3-c]pyridine-3-carboxamide hydrochloride, N-(4-methylcyclohexyl)-1,2,3,4-tetrahydrobenzo[b]thieno[2,3-c]pyridine-3-carboxamide hydrochloride, N-(2-methylcyclohexyl)-1,2,3,4-tetrahydrobenzo[b]thieno[2,3-c]pyridine-3-carboxamide hydrochloride, N-(4-tert-butylcyclohexyl)-1,2,3,4-tetrahydrobenzo[b]thieno[2,3-c]pyridine-3-carboxamide hydrochloride, N-(4-aminocyclohexyl)-1,2,3,4-tetrahydrobenzo[b]thieno[2,3-c]pyridine-3-carboxamide trihydrochloride, N-piperidino-1,2,3,4-tetrahydrobenzo[b]thieno[2,3-c]pyridine-3-carboxamide dihydrochloride, N-{1-(4-methylpiperazinyl)}-1,2,3,4-tetrahydrobenzo[b]thieno[2,3-c]pyridine-3-carboxamide trihydrochloride, N-(2,6-dimethylpiperidino)-1,2,3,4-tetrahydrobenzo[b]thieno[2,3-c]pyridine-3-carboxamide dihydrochloride, N-(1-pyrrolidinyl)-1,2,3,4-tetrahydrobenzo[b]thieno[2,3-c]pyridine-3-carboxamide dihydrochloride, N-[1-{4-(2-hydroxyethyl)piperazinyl}]-1,2,3,4-tetrahydrobenzo[b]thieno[2,3-c]pyridine-3-carboxamide trihydrochloride, N-{4-(1,2-diethylpyrazolidinyl)}-1,2,3,4-tetrahydrobenzo[b]thieno[2,3-c]pyridine-3-carboxamide trihydrochloride, N-cyclohexyl-N-methyl-1,2,3,4-tetrahydrobenzo[b]thieno[2,3-c]pyridine-3-carboxamide hydrochloride, N-(4-pyridyl)-1,2,3,4-tetrahydrobenzo[b]thieno[2,3-c]pyridine-3-carboxamide hydrochloride, N-phenyl-1,2,3,4-tetrahydrobenzo[b]thieno[2,3-c]pyridine-3-carboxamide hydrochloride, N-(1-pyrrolinyl)-1,2,3,4-tetrahydrobenzo[b]thieno[2,3-c]pyridine-3-carboxamide hydrochloride, N-{4-(1,2,4-triazolyl)}-1,2,3,4-tetrahydrobenzo[b]thieno[2,3-c]pyridine-3-carboxamide hydrochloride, N-cyclooctyl-1,2,3,4-tetrahydrobenzo[b]thieno[2,3-c]pyridine-3-carboxamide hydrochloride, N-(4-piperidinyl)methyl-1,2,3,4-tetrahydrobenzo[b]thieno[2,3-c]pyridine-3-carboxamide dihydrochloride, N-cyclohexylmethyl-1,2,3,4-tetrahydrobenzo[b]thieno[2,3-c]pyridine-3-carboxamide hydrochloride, N-(3-pentyl)-1,2,3,4-tetrahydrobenzo[b]thieno[2,3-c]pyridine-3-carboxamide hydrochloride, N-diethyl-1,2,3,4-tetrahydrobenzo[b]thieno[2,3-c]pyridine-3-carboxamide hydrochloride, N-(1-adamantyl)-1,2,3,4-tetrahydrobenzo[b]thieno[2,3-c]pyridine-3-carboxamide hydrochloride, N-(3-quinuclidinyl)-1,2,3,4-tetrahydrobenzo[b]thieno[2,3-c]pyridine-3-carboxamide dihydrochloride, N-(exo-2-norbornyl)-1,2,3,4-tetrahydrobenzo[b]thieno[2,3-c]pyridine-3-carboxamide hydrochloride, 1-(3-chlorophenyl)-4-{3-(1,2,3,4-tetrahydrobenzo[b]thieno[2,3-c]pyridine)carbonyl}piperazine dihydrochloride, N-piperonyl-1,2,3,4-tetrahydrobenzo[b]thieno[2,3-c]pyridine-3-carboxamide hydrochloride, N-(2-methoxybenzyl)-1,2,3,4-tetrahydrobenzo[b]thieno[2,3-c]pyridine-3-carboxamide hydrochloride, N-(3-methoxybenzyl)-1,2,3,4-tetrahydrobenzo[b]thieno[2,3-c]pyridine-3-carboxamide hydrochloride, N-(4-methoxybenzyl)-1,2,3,4-tetrahydrobenzo[b]thieno[2,3-c]pyridine-3-carboxamide hydrochloride, N-(2,3-dimethoxybenzyl)-1,2,3,4-tetrahydrobenzo[b]thieno[2,3-c]pyridine-3-carboxamide hydrochloride, N-(2,4-dimethoxybenzyl)-1,2,3,4-tetrahydrobenzo[b]thieno[2,3-c]pyridine-3-carboxamide hydrochloride, N-(3,4-dimethoxybenzyl)-1,2,3,4-tetrahydrobenzo[b]thieno[2,3-c]pyridine-3-carboxamide hydrochloride, N-(3,5-dimethoxybenzyl)-1,2,3,4-tetrahydrobenzo[b]thieno[2,3-c]pyridine-3-carboxamide hydrochloride, N-(2,4,6-trimethoxybenzyl)-1,2,3,4-tetrahydrobenzo[b]thieno[2,3-c]pyridine-3-carboxamide hydrochloride, N-(3,4,5-trimethoxybenzyl)-1,2,3,4-tetrahydrobenzo[b]thieno[2,3-c]pyridine-3-carboxamide hydrochloride, N-(α-methylbenzyl)-1,2,3,4-tetrahydrobenzo[b]thieno[2,3-c]pyridine-3-carboxamide hydrochloride, N-(4-methylbenzyl)-1,2,3,4-tetrahydrobenzo[b]thieno[2,3-c]pyridine-3-carboxamide hydrochloride, N-[4-(trifluoromethyl)benzyl]-1,2,3,4-tetrahydrobenzo[b]thieno[2,3-c]pyridine-3-carboxamide hydrochloride, N-[4-(isopropyl)benzyl]-1,2,3,4-tetrahydrobenzo[b]thieno[2,3-c]pyridine-3-carboxamide hydrochloride, N-[4-(tert-butyl)benzyl]-1,2,3,4-tetrahydrobenzo[b]thieno[2,3-c]pyridine-3-carboxamide hydrochloride, N-[4-(isopropyl)phenyl]-1,2,3,4-tetrahydrobenzo[b]thieno[2,3-c]pyridine-3-carboxamide hydrochloride, N-[4-(tert-butyl)phenyl]-1,2,3,4-tetrahydrobenzo[b]thieno[2,3-c]pyridine-3-carboxamide hydrochloride, N-[trans-2-(phenylcyclopropyl)]-1,2,3,4-tetrahydrobenzo[b]thieno[2,3-c]pyridine-3-carboxamide hydrochloride, N-ethynylcyclohexyl-1,2,3,4-tetrahydrobenzo[b]thieno[2,3-c]pyridine-3-carboxamide hydrochloride, N-cyclononyl-1,2,3,4-tetrahydrobenzo[b]thieno[2,3-c]pyridine-3-carboxamide hydrochloride, N-cyclodecanyl-1,2,3,4-tetrahydrobenzo[b]thieno[2,3-c]pyridine-3-carboxamide hydrochloride, N-(2,3-dimethylcyclohexyl)-1,2,3,4-tetrahydrobenzo[b]thieno[2,3-c]pyridine-3-carboxamide hydrochloride, N-(tert-butyl)-1,2,3,4-tetrahydrobenzo[b]thieno[2,3-c]pyridine-3-carboxamide hydrochloride, N-(isoamyl)-1,2,3,4-tetrahydrobenzo[b]thieno[2,3-c]pyridine-3-carboxamide hydrochloride, N-[(−)-cis-myrtanyl]-1,2,3,4-tetrahydrobenzo[b]thieno[2,3-c]pyridine-3-carboxamide hydrochloride, N-(endo-2-norbonyl)-1,2,3,4-tetrahydrobenzo[b]thieno[2,3-c]pyridine-3-carboxamide hydrochloride, N-cyclododecyl-1,2,3,4-tetrahydrobenzo[b]thieno[2,3-c]pyridine-3-carboxamide hydrochloride, N-(isobutyl)-1,2,3,4-tetrahydrobenzo[b]thieno[2,3-c]pyridine-3-carboxamide hydrochloride, N-diisopropyl-1,2,3,4-tetrahydrobenzo[b]thieno[2,3-c]pyridine-3-carboxamide hydrochloride, N-(1,3-dimethylbutyl)-1,2,3,4-tetrahydrobenzo[b]thieno[2,3-c]pyridine-3-carboxamide hydrochloride, N-(2-heptyl)-1,2,3,4-tetrahydrobenzo[b]thieno[2,3-c]pyridine-3-carboxamide hydrochloride, N-(4-heptyl)-(1,2,3,4-tetrahydrobenzo[b]thieno[2,3-c]pyridine)carboxamide hydrochloride, N-(2-octyl)-1,2,3,4-tetrahydrobenzo[b]thieno[2,3-c]pyridine-3-carboxamide hydrochloride, N-(sec-butyl)-1,2,3,4-tetrahydrobenzo[b]thieno[2,3-c]pyridine-3-carboxamide hydrochloride, N-(2-pentyl)-1,2,3,4-tetrahydrobenzo[b]thieno[2,3-c]pyridine-3-carboxamide hydrochloride, N-(tert-amyl)-1,2,3,4-tetrahydrobenzo[b]thieno[2,3-c]pyridine-3-carboxamide hydrochloride, N-(1,2-dimethylpropyl)-1,2,3,4-tetrahydrobenzo[b]thieno[2,3-c]pyridine-3-carboxamide hydrochloride, N-(1,5-dimethylhexyl)-1,2,3,4-tetrahydrobenzo[b]thieno[2,3-c]pyridine-3-carboxamide hydrochloride, N-(2-ethylhexyl)-1,2,3,4-tetrahydrobenzo[b]thieno[2,3-c]pyridine-3-carboxamide hydrochloride, N-(1,1,3,3-tetramethylbutyl)-1,2,3,4-tetrahydrobenzo[b]thieno[2,3-c]pyridine-3-carboxamide hydrochloride, N-octyl-1,2,3,4-tetrahydrobenzo[b]thieno[2,3-c]pyridine-3-carboxamide hydrochloride, N-[(S)-(−)-2-methylbutyl]-1,2,3,4-tetrahydrobenzo[b]thieno[2,3-c]pyridine-3-carboxamide hydrochloride and N-(3,3-dimethylpropyl)-1,2,3,4-tetrahydrobenzo[b]thieno[2,3-c]pyridine-3-carboxamide hydrochloride.

Also, the procedure of the above Example 1 was repeated except for replacing 0.99 g of the trans-4-hydroxycyclohexylamine hydrochloride employed in Example 1 with each of the corresponding alcohol compounds and replacing 1.98 g of the diphenylphosphoryl azide employed as a condensing agent with 1.48 g of 1,3-dicyclohexylcarbodiimide to give thereby cyclohexyl 1,2,3,4-tetrahydrobenzo[b]thieno[2,3-c]pyridine-3-carboxylate hydrochloride, cyclopentyl 1,2,3,4-tetrahydrobenzo[b]thieno[2,3-c]pyridine-3-carboxylate hydrochloride, cycloheptyl 1,2,3,4-tetrahydrobenzo[b]thieno[2,3-c]pyridine-3-carboxylate hydrochloride, cyclooctyl 1,2,3,4-tetrahydrobenzo[b]thieno[2,3-c]pyridine-3-carboxylate hydrochloride and N-cyclohexylmethyl 1,2,3,4-tetrahydrobenzo[b]thieno[2,3-c]pyridine-3-carboxylate hydrochloride.

In the case of N-cyclohexyl-6-hydroxy-1,2,3,4-tetrahydrobenzo[b]thieno[2,3-c]pyridine-3-carboxamide hydrochloride, 32.3 g of the 3-chloromethylbenzo[b]thiophene was replaced with 35.1 g of 6-hydroxy-3-chloromethylbenzo[b]thiophene.

Tables 5 to 23 show the results while Tables 24 to 39 show the analytical data.

TABLE 5

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 2-hydroxycyclo-hexylamine hydrochloride 0.99 g | room temp. | 1 day | 1.11 g (51%) | N-(2-hydroxycylohexyl)-1,2,3,4-tetrahydro-benzo[b]thieno[2,3-c]-pyridine-3-carboxamide hydrochloride |
| 2.0 g | 4-methylcyclo-hexylamine 0.74 g | room temp. | 1 day | 1.28 g (59%) | N-(4-methylcyclohexyl)-1,2,3,4-tetrahydro-benzo[b]thieno[2,3-c]-pyridine-3-carboxamide hydrochloride |
| 2.0 g | 2-methylcyclo-hexylamine 0.74 g | room temp. | 1 day | 1.20 g (58%) | N-(2-methylcylohexyl)-1,2,3,4-tetrahydro-benzo[b]thieno[2,3-c]-pyridine-3-carboxamide hydrochloride |
| 2.0 g | 4-tert-butyl-cyclohexylamine 1.0 g | room temp. | 1 day | 1.48 g (61%) | N-(4-tert-butylcyclo-hexyl)-1,2,3,4-tetra-hydrobenzo[b]thieno-(2,3-c]pyridine-3-carboxamide hydrochloride |

TABLE 6

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 4-aminocyclo-hexylamine 0.75 g | room temp. | 1 day | 1.17 g (45%) | N-(4-aminocylohexyl)-1,2,3,4-tetrahydro-benzo[b]thieno[2,3-c]-pyridine-3-carboxamide trihydrochloride |
| 2.0 g | 1-amino-piperidine 0.65 g | room temp. | 1 day | 0.85 g (37%) | N-piperidino-1,2,3,4-tetrahydrobenzo[b]-thieno[2,3-c)pyridine-3-carboxamide dihydrochloride |
| 2.0 g | 1-amino-4-methyl-piperazine 0.75 g | room temp. | 1 day | 0.89 g (34%) | N-{1-(4-methyl-piperazinyl)}-1,2,3,4-tetrahydrobenzo[b]-thieno[2,3-c]pyridine-3-carboxamide trihydrochloride |
| 2.0 g | 1-amino-2,6-di-methyl-piperidine 0.80 g | room temp. | 1 day | 1.17 g (48%) | N-(2,6-dimethyl-piperidine)-1,2,3,4-tetrahydrobenzo[b]-thieno[2,3-c]pyridine-3-carboxamide dihydrochloride |

TABLE 7

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 1-amino-pyrrolidine hydrochloride 0.80 g | room temp. | 1 day | 1.38 g (62%) | N-(1-pyrrolidinyl)-1,2,3,4-tetrahydro-benzo[b]thieno[2,3-c]-pyridine-3-carboxamide dihydrochloride |
| 2.0 g | 1-amino-4-(2- | room temp. | 1 day | 0.22 g | N-[1-{4-(2-hydroxy- |

TABLE 7-continued

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| | hydroxyethyl)-piperazine 0.95 g | temp. | | (8%) | ethyl)-piperazinyl}]-1,2,3,4-tetrahydrobenzo-[b]thieno[2,3-c]-pyridine-3-carboxamide trihydrochloride |
| 2.0 g | 4-amino-1,2-diethyl-pyrazolidine 0.61 g | room temp. | 1 day | 1.64 g (59%) | N-{4-(1,2-diethyl-pyrazolidinyl)}-1,2,3,4-tetrahydrobenzo[b]-thieno[2,3-c]pyridine-3-carboxamide trihydrochloride |
| 2.0 g | N-cyclohexyl-N-methylamine 0.69 g | room temp. | 1 day | 1.28 g (59%) | N-cyclohexyl-N-methyl-1,2,3,4-tetrahydro-benzo[b]thieno[2,3-c]-pyridine-3-carboxamide hydrochloride |

TABLE 8

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 4-aminopyridine 0.61 g | room temp. | 1 day | 1.04 g (51%) | N-(4-pyridyl)-1,2,3,4-tetrahydrobenzo[b]-thieno[2,3-c]pyridine-3-carboxamide hydrochloride |
| 2.0 g | aniline 0.61 g | room temp. | 1 day | 1.68 g (82%) | N-phenyl-1,2,3,4-tetrahydrobenzo[b]-thieno[2,3-c]pyridine-3-carboxamide hydrochloride |
| 2.0 g | 1-aminopyrrole 0.54 g | room temp. | 1 day | 730 mg (37%) | N-(1-pyrrolinyl)-1,2,3,4-tetrahydro-benzo[b]thieno[2,3-c]-pyridine-3-carboxamide hydrochloride |
| 2.0 g | 4-amino-1,2,4-triazoline 0.55 g | room temp. | 1 day | 695 mg (35%) | N-{4-(1,2,4-triazolyl)}-1,2,3,4-tetrahydro-benzo[b]thieno[2,3-c]-pyridine-3-carboxamide hydrochloride |

TABLE 9

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | cyclooctylamine 0.83 g | room temp. | 1 day | 1.33 g (59%) | N-cyclooctyl-1,2,3,4-tetrahydrobenzo[b]-thieno[2,3-c]pyridine-3-carboxamide hydrochloride |
| 2.0 g | 4-aminomethyl piperidine 0.76 g | room temp. | 1 day | 1.46 g (61%) | N-(4-piperidinyl)methyl-1,2,3,4-tetrahydro-benzo[b]thieno[2,3-c]-pyridine-3-carboxamide dihydrochloride |
| 2.0 g | cyclohexyl-methylamine 0.75 g | room temp. | 1 day | 1.36 g (63%) | N-cyclohexylmethyl-1,2,3,4-tetrahydro-benzo[b]thieno[2,3-c]- |

TABLE 9-continued

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 3-pentylamine 0.58 g | room temp. | 1 day | 1.19 g (59%) | pyridine-3-carboxamide hydrochloride N-(3-pentyl)-1,2,3,4-tetrahydrobenzo[b]-thieno[2,3-c]pyridine-3-carboxamide hydrochloride |

TABLE 10

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | diethylamine 0.49 g | room temp. | 1 day | 873 mg (51%) | N-diethyl-1,2,3,4-tetrahydrobenzo[b]-thieno[2,3-c]pyridine-3-carboxamide hydrochloride |
| 2.0 g | 1-adamantyl-amine hydrochloride 1.25 g | room temp. | 1 day | 1.99 g (83%) | N-(1-adamantyl)-1,2,3,4-tetrahydrobenzo[b]-thieno[2,3-c]pyridine-3-carboxamide hydrochloride |
| 2.0 g | 3-amino-quinuclidine dihydrochloride 1.33 g | room temp. | 1 day | 727 mg (36%) | N-(3-quinuclidinyl)-1,2,3,4-tetrahydro-benzo[b]thieno[2,3-c]-pyridine-3-carboxamide dihydrochloride |
| 2.0 g | exo-2-amino-norbornane 0.74 g | room temp. | 1 day | 0.81 g (34%) | N-(2-exo-norbonyl)-1,2,3,4-tetrahydro-benzo[b]thieno[2,3-c]pyridine-3-carboxamide hydrochloride |

TABLE 11

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 3-chlorophenyl piperazine hydrochloride 1.55 g | room temp. | 1 day | 2.45 g (85%) | 1-(3-chlorophenyl)-4-{3-(1,2,3,4-tetrahydro-benzo[b]thieno[2,3-c]-pyridine)-3-carbonyl}-piperazine dihydrochloride |
| 2.0 g | piperonylamine 1.01 g | room temp. | 1 day | 1.66 g (69%) | N-piperonyl-1,2,3,4-tetrahydrobenzo[b]-thieno[2,3-c]pyridine-3-carboxamide hydrochloride |
| 2.0 g | 2-methoxy-benzylamine 0.92 g | room temp. | 1 day | 1.62 g (70%) | N-(2-methoxybenzyl)-1,2,3,4-tetrahydro-benzo[b]thieno[2,3-c]-pyridine-3-carboxamide hydrochloride |
| 2.0 g | 3-methoxy-benzylamine 0.92 g | room temp. | 1 day | 1.69 g (73%) | N-(3-methoxybenzyl) 1,2,3,4-tetrahydro-benzo[b]thieno[2,3-c]pyridine-3-carboxamide hydrochloride |

TABLE 12

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 4-methoxy-benzylamine 0.92 g | room temp. | 1 day | 1.53 g (66%) | N-(4-methoxybenzyl)-1,2,3,4-tetrahydro-benzo[b]thieno[2,3-c]-pyridine-3-carboxamide hydrochloride |
| 2.0 g | 2,3-dimethoxy-benzylamine 1.12 g | room temp. | 1 day | 1.73 g (69%) | N-(2,3-dimethoxybenzyl)-1,2,3,4-tetrahydro-benzo[b]thieno[2,3-c]-pyridine-3-carboxamide hydrochloride |
| 2.0 g | 2,4-dimethoxy-benzylamine 1.12 g | room temp. | 1 day | 1.80 g (72%) | N-(2,4-dimethoxybenzyl)-1,2,3,4-tetrahydro-benzo[b]thieno[2,3-c]-pyridine-3-carboxamide hydrochloride |
| 2.0 g | 3,4-dimethoxy-benzylamine 1.12 g | room temp. | 1 day | 1.63 g (65%) | N-(3,4-dimethoxybenzyl)-1,2,3,4-tetrahydro-benzo[b]thieno[2,3-c]pyridine-3-carboxamide hydrochloride |

TABLE 13

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 3,5-dimethoxy-benzylamine 1.12 g | room temp. | 1 day | 1.85 g (69%) | N-(3,5-dimethoxybenzyl)-1,2,3,4-tetrahydro-benzo[b]thieno[2,3-c]-pyridine-3-carboxamide hydrochloride |
| 2.0 g | 2,4,6-tri-methoxybenzyl-amine 1.32 g | room temp. | 1 day | 1.96 g (73%) | N-(2,4,6-trimethoxy-benzyl)-1,2,3,4-tetrahydrobenzo[b]-thieno[2,3-c]pyridine-3-carboxamide hydrochloride |
| 2.0 g | 3,4,5-tri-methoxybenzyl-amine 1.32 g | room temp. | 1 day | 1.76 g (70%) | N-(3,4,5-trimethoxy-benzyl)-1,2,3,4-tetra-hydrobenzo[b]thieno[2,3-c]pyridine-3-carboxamide hydrochloride |
| 2.0 g | α-methylbenzyl-amine 0.89 g | room temp. | 1 day | 1.32 g (60%) | N-(α-methylbenzyl)-1,2,3,4-tetrahydro-benzo[b]thieno[2,3-c]pyridine-3-carboxamide hydrochloride |

TABLE 14

| 2-Tert-butoxy-carbonyl-1,2,3,4-tetrahydrobenzo[b]-thieno[2,3-c]-pyridinecarboxyic acid | Amino compound | Reaction temperature | Reaction time | Final yield | Final product |
|---|---|---|---|---|---|
| 2.0 g | 4-methylbenzyl-amine 0.89 g | room temp. | 1 day | 1.39 g (63%) | N-(4-methylbenzyl)-1,2,3,4-tetrahydro-benzo[b]thieno[2,3-c]-pyridine-3-carboxamide hydrochloride |
| 2.0 g | 4-(trifluoro-methyl)benzyl-amine | room temp. | 1 day | 1.42 g (56%) | N-[4-(trifluoromethyl)-benzyl]-1,2,3,4-tetra-hydrobenzo[b]thieno[2,3- |

TABLE 14-continued

| 2-Tert-butoxy-carbonyl-1,2,3,4-tetrahydrobenzo[b]-thieno[2,3-c]-pyridinecarboxyic acid | Amino compound | Reaction temperature | Reaction time | Final yield | Final product |
|---|---|---|---|---|---|
| | 1.28 g | | | | c]pyridine-3-carboxamide hydrochloride |
| 2.0 g | 4-(isopropyl)-benzylamine 1.09 g | room temp. | 1 day | 1.45 g (63%) | N-[4-(isopropyl)-benzyl]-1,2,3,4-tetra-hydrobenzo[b]thieno[2,3-c]pyridine-3-carboxamide hydrochloride |
| 2.0 g | 4-(tert-butyl)-benzylamine 1.19 g | room temp. | 1 day | 1.35 g (55%) | N-[4-(tert-butyl)-benzyl]-1,2,3,4-tetra-hydrobenzo[b]thieno-[2,3-c]pyridine-3-carboxamide hydrochloride |

TABLE 15

| 2-Tert-butoxy-carbonyl-1,2,3,4-tetrahydrobenzo[b]-thieno[2,3-c]-pyridinecarboxyic acid | Amino compound | Reaction temperature | Reaction time | Final yield | Final product |
|---|---|---|---|---|---|
| 2.0 g | 4-isopropyl-aniline 0.99 g | room temp. | 1 day | 1.37 g (60%) | N-[4-(isopropyl)-phenyl]-1,2,3,4-tetra-hydrobenzo[b]thieno[2,3-c]pyridine-3-carboxamide hydrochloride |
| 2.0 g | 4-tert-butyl-aniline 1.09 g | room temp. | 1 day | 1.49 g (63%) | N-[4-(tert-butyl)-phenyl]-1,2,3,4-tetrahydrobenzo[b]-thieno[2,3-c]pyridine-3-carboxamide hydrochloride |
| 2.0 g | trans-2-phenyl-cyclopropyl-amine 0.97 g | room temp. | 1 day | 1.39 g (61%) | N-[trans-2-(phenylcyclo-propyl)]-1,2,3,4-tetra-hydrobenzo[b]thieno[2,3-c]pyridine-3-carboxamide hydrochloride |
| 2.0 g | 1-ethynylcyclo-hexylamine 0.90 g | room temp. | 1 day | 1.31 g (59%) | N-ethynylcyclohexyl-1,2,3,4-tetrahydro-benzo[b]thieno[2,3-c]pyridine-3-carboxamide hydrochloride |

TABLE 16

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | cyclononylamine 1.03 g | room temp. | 1 day | 1.51 g (65%) | N-cyclonynyl-1,2,3,4-tetrahydrobenzo[b]thieno[2,3-c]pyridine-3-carboxamide hydrochloride |
| 2.0 g | cyclodecanyl-amine 1.14 g | room temp. | 1 day | 1.23 g (51%) | N-cyclodecanyl-1,2,3,4-tetrahydrobenzo[b]-thieno[2,3-c]pyridine-3-carboxamide hydrochloride |
| 2.0 g | 2,3-dimethyl-cyclohexylamine 0.93 g | room temp. | 1 day | 1.26 g (56%) | N-(2,3-dimethylcyclo-hexyl)-1,2,3,4-tetra-hydrobenzo[b]thieno[2,3-c]pyridine-3-carboxamide hydrochloride |

TABLE 16-continued

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | tert-butylamine 0.54 g | room temp. | 1 day | 0.94 g (49%) | N-(tert-butyl)-1,2,3,4-tetrahydrobenzo[b]-thieno[2,3-c]pyridine-3-carboxamide hydrochloride |

TABLE 17

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | isoamylamine 0.64 g | room temp. | 1 day | 0.90 g (45%) | N-(isoamyl)-1,2,3,4-tetrahydrobenzo[b]-thieno[2,3-c]pyridine-3-carboxamide hydrochloride |
| 2.0 g | (−)-cis-myrtanylamine 1.12 g | room temp. | 1 day | 1.05 g (44%) | N-[(−)-cis-myrtanyl]-1,2,3,4-tetrahydro-benzo[b]thieno[2,3-c]-pyridine-3-carboxamide hydrochloride |
| 2.0 g | endo-2-amino-norbornane 1.08 g | room temp. | 1 day | 0.99 g (46%) | N-(endo-2-norbornyl)-1,2,3,4-tetrahydro-benzo[b]thieno[2,3-c]pyridine-3-carboxamide hydrochloride |
| 2.0 g | cyclododecyl-amine 1.34 g | room temp. | 1 day | 1.44 g | N-cyclododecyl-1,2,3,4-tetrahydrobenzo[b]-thieno[2,3-c]pyridine-3-carboxamide hydrochloride |

TABLE 18

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | isobutylamine 0.49 g | room temp. | 1 day | 0.94 g (49%) | N-(isobutyl)-1,2,3,4-tetrahydrobenzo[b]-thieno[2,3-c]pyridine-3-carboxamide hydrochloride |
| 2.0 g | diisopropyl-amine 0.67 g | room temp. | 1 day | 1.06 g (51%) | N-diisopropyl-1,2,3,4-tetrahydrobenzo[b]-thieno[2,3-c]pyridine-3-carboxamide hydrochloride |
| 2.0 g | 1,3-dimethyl-butylamine 0.67 g | room temp. | 1 day | 1.15 g (55%) | N-(1,3-dimethylbutyl)-1,2,3,4-tetrahydro-benzo[b]thieno[2,3-c]-pyridine-3-carboxamide hydrochloride |
| 2.0 g | 2-heptylamine 0.77 g | room temp. | 1 day | 1.00 g (46%) | N-(2-heptyl)-1,2,3,4-tetrahydrobenzo[b]-thieno[2,3-c]pyridine-3-carboxamide hydrochloride |

TABLE 19

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 4-heptylamine 0.77 g | room temp. | 1 day | 0.89 g (41%) | N-(4-heptyl)-1,2,3,4-tetrahydrobenzo[b]-thieno[2,3-c]pyridine-3-carboxamide hydrochloride |
| 2.0 g | 2-octylamine 0.86 g | room temp. | 1 day | 1.01 g (45%) | N-(2-octyl)-1,2,3,4-tetrahydrobenzo[b]-thieno[2,3-c]pyridine-3-carboxamide hydrochloride |
| 2.0 g | sec-butylamine 0.49 g | room temp. | 1 day | 0.84 g (44%) | N-(sec-butyl)-1,2,3,4-tetrahydrobenzo[b]-thieno[2,3-c]pyridine-3-carboxamide hydrochloride |
| 2.0 g | 2-pentylamine 0.58 g | room temp. | 1 day | 1.07 g (52%) | N-(2-pentyl)-1,2,3,4-tetrahydrobenzo[b]-thieno[2,3-c]pyridine-3-carboxamide hydrochloride |

TABLE 20

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | tert-amylamine 0.58 g | room temp. | 1 day | 1.12 g (56%) | N-(tert-amyl)-1,2,3,4-tetrahydrobenzo[b]-thieno[2,3-c]pyridine-3-carboxamide hydrochloride |
| 2.0 g | 1,2-dimethyl-propylamine 0.58 g | room temp. | 1 day | 0.94 g (47%) | N-(1,2-dimethylpropyl)-1,2,3,4-tetrahydro-benzo[b]thieno[2,3-c]-pyridine-3-carboxamide hydrochloride |
| 2.0 g | 1,5-dimethyl-hexylamine 0.86 g | room temp. | 1 day | 1.10 g (49%) | N-(1,5-dimethylhexyl)-1,2,3,4-tetrahydro-benzo[b]thieno[2,3-c]-pyridine-3-carboxamide hydrochloride |
| 2.0 g | 2-ethylhexyl-amine 0.86 g | room temp. | 1 day | 1.06 g (47%) | N-(2-ethylhexyl)-1,2,3,4-tetrahydro-benzo[b]thieno[2,3-c]-pyridine-3-carboxamide hydrochloride |

TABLE 21

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 1,1,3,3-tetra-methylbutyl-amine 0.86 g | room temp. | 1 day | 1.15 g (51%) | N-(1,1,3,3-tetramethyl-butyl)-1,2,3,4-tetra-hydrobenzo[b]thieno[2,3-c]pyridine-3-carboxamide hydrochloride |
| 2.0 g | octylamine 0.86 g | room temp. | 1 day | 1.28 g (57%) | N-octyl-1,2,3,4-tetra-hydrobenzo[b]thieno[2,3-c]pyridine-3-carboxamide hydrochloride |
| 2.0 g | (S)-(−)-2-methylbutyl-amine 0.58 g | room temp. | 1 day | 0.88 g (44%) | N-[(S)-(−)-2-methyl-butyl]-1,2,3,4-tetra-hydrobenzo[b]thieno[2,3-c]pyridine-3-carboxamide hydrochloride |

TABLE 21-continued

| 2-Tert-butoxy-carbonyl-1,2,3,4-tetrahydrobenzo[b]-thieno[2,3-c]-pyridinecarboxylic acid | Amino compound | Reaction temperature | Reaction time | Final yield | Final product |
|---|---|---|---|---|---|
| 2.0 g | 3,3-dimethyl-propylamine 0.58 g | room temp. | 1 day | 1.04 g (52%) | N-(3,3-dimethylpropyl)-1,2,3,4-tetrahydro-benzo[b]thieno[2,3-c]-pyridine-3-carboxamide hydrochloride |

TABLE 22

| 2-Tert-butoxy-carbonyl-1,2,3,4-tetrahydrobenzo[b]-thieno[2,3-c]-pyridinecarboxylic acid | Alcohol compound | Reaction temperature | Reaction time | Final yield | Final product |
|---|---|---|---|---|---|
| 2.0 g | cyclohexanol 0.65 g | room temp. | 1 day | 1.65 g (77%) | cyclohexyl 1,2,3,4-tetrahydrobenzo[b]-thieno[2,3-c]pyridine-3-carboxylate hydrochloride |
| 2.0 g | cyclopentanol 0.56 g | room temp. | 1 day | 1.24 g (70%) | cyclopentyl 1,2,3,4-tetrahydrobenzo[b]-thieno[2,3-c]pyridine-3-carboxylate hydrochloride |
| 2.0 g | cycloheptanol 0.74 g | room temp. | 1 day | 1.41 g (65%) | cycloheptyl 1,2,3,4-tetrahydrobenzo[b]-thieno[2,3-c]pyridine-3-carboxylate hydrochloride |
| 2.0 g | cyclooctanol 0.83 g | room temp. | 1 day | 1.37 g (61%) | cyclooctyl 1,2,3,4-tetrahydrobenzo[b]-thieno[2,3-c]pyridine-3-carboxylate hydrochloride |

TABLE 23

| 2-Tert-butoxy-carbonyl-1,2,3,4-tetrahydrobenzo[b]-thieno[2,3-c]-pyridinecarboxylic acid | | Reaction temperature | Reaction time | Final yield | Final product |
|---|---|---|---|---|---|
| | Alcohol compound | | | | |
| 2.0 g | cyclohexyl methanol 0.75 g | room temp. | 1 day | 1.06 g (49%) | cyclohexylmethyl 1,2,3,4-tetrahydro-benzo[b]thieno[2,3-c]pyridine-3-carboxylate hydrochloride |
| | Amino compound | | | | |
| 2.0 g | cyclohexylamine 0.65 g | room temp. | 1 day | 480 mg (22%) | N-cyclohexyl-6-hydroxy-1,2,3,4-tetrahydro-benzo[b]thieno[2,3-c]pyridine-3-carboxamide hydrochloride |

TABLE 24

| Final compound | IR ($V_{max}$, cm$^{-1}$) | NMR (δ, $CD_3OD$) | Mass (m/z) |
|---|---|---|---|
| N-(2-hydroxycyclohexyl)-1,2,3,4-tetrahydrobenzo[b]thieno[2,3-c]-pyridine-3-carboxamide | 2925, 1670, 1550, 1435, 755 | 0.91–2.14(m, 10H), 3.10–4.63(m, 5H), 7.10–7.95(m, 4H) | 331, 188 |

TABLE 24-continued

| Final compound | IR ($V_{max}$, cm$^{-1}$) | NMR (δ, CD$_3$OD) | Mass (m/z) |
|---|---|---|---|
| hydrochloride | | | |
| N-(4-methylcyclohexyl)-1,2,3,4-tetrahydrobenzo[b]thieno[2,3-c]-pyridine-3-carboxamide hydrochloride | 3325, 2940 1670, 1555, 1435, 760 | 0.70–3.03(m, 13H), 2.77–4.07(m, 5H), 7.20–8.03(m, 4H) | 329, 188 |
| N-(2-methylcyclohexyl)-1,2,3,4-tetrahydrobenzo[b]thieno[2,3-c]-pyridine-3-carboxamide hydrochloride | 2900, 1655, 1530, 1420, 750 | 0.73–2.13(m, 13H), 2.47–3.67(m, 5H), 7.23–8.10(m, 4H) | 329, 188 |
| N-(4-tert-butylcyclohexyl)-1,2,3,4-tetrahydrobenzo[b]thieno[2,3-c]-pyridine-3-carboxamide hydrochloride | 1655, 1560, 1430, 755 | 0.60–2.33(m, 10H), 0.85(s, 9H), 2.67–3.87(m, 5H), 7.20–7.87(m, 4H) | 371, 188 |
| N-(4-aminocyclohexyl)-1,2,3,4-tetrahydrobenzo[b]thieno[2,3-c]-pyridine-3-carboxamide trihydrochloride | 2920, 1680, 1550, 1438, 760 | 1.10–2.52(m, 10H), 2.86–4.10(m, 5H), 7.48–8.33(m, 4H) | 330, 312, 188 |

TABLE 25

| Final compound | IR ($V_{max}$, cm$^{-1}$) | NMR (δ, CD$_3$OD) | Mass (m/z) |
|---|---|---|---|
| N-piperidino-1,2,3,4-tetrahydrobenzo[b]thieno[2,3-c]pyridine-3-carboxamide dihydrochloride | 1715, 1370, 760 | 1.50–2.37(m, 10H), 3.33–4.70(m, 5H), 7.37–8.10(m, 4H) | 316, 231, 188 |
| N-{1-(4-methylpiperazinyl)}-1,2,3,4-tetrahydrobenzo[b]thieno[2,3-c]-pyridine-3-carboxamide trihydrochloride | 1680, 1430, 760 | 2.30(2, 3H), 2.47–4.80(m, 13H), 7.17–7.87(m, 4H) | 331, 188 |
| N-(2,6-dimethylpiperidino)-1,2,3,4-tetrahydrobenzo[b]thieno[2,3-c]-pyridine-3-carboxamide dihydrochloride | 2950, 1680, 1425, 755 | 1.05(d, J=6Hz, 6H), 2.45–4.20(m, 13H), 7.20–7.92(m, 4H) | 336, 188 |
| N-(1-pyrrolidinyl)-1,2,3,4-tetrahydrobenzo[b]thieno[2,3-c]-pyridine-3-carboxamide dihydrochloride | 1705, 1560, 1430, 760 | 1.60–4.47(m, 13H), 7.20–8.00(m, 4H) | 303, 231, 188 |
| N-[1-{4-(2-hydroxyethyl)-piperazinyl}]-1,2,3,4-tetrahydrobenzo[b]thieno[2,3-c]pyridine-3-carboxamide trihydrochloride | 2900, 1660, 1420, 1260, 760 | 2.93(s, 3H), 3.13–4.30(m, 13H), 7.17–7.97(m, 4H) | 316, 298, 188 |

TABLE 26

| Final compound | IR ($V_{max}$, cm$^{-1}$) | NMR (δ, CD$_3$OD) | Mass (m/z) |
|---|---|---|---|
| N-{4-(1,2-diethylpyrazolidinyl)}-1,2,3,4-tetrahydrobenzo[b]thieno-[2,3-c]pyridine-3-carboxamide trihydrochloride | 3200, 1680, 1550, 1430, 760 | 1.07(t, J=6Hz, 6H), 2.67(q=6Hz, 4H), 1.37–4.93(m, 10H) 7.07–7.90(m, 4H) | 359 |
| N-cyclohexyl-N-methyl-1,2,3,4-tetrahydrobenzo[b]thieno[2,3-c]-pyridine-3-carboxamide hydrochloride | 2970, 1660, 1440, 760 | 0.68–2.36(m, 11H), 2.64–4.20(m, 5H), 2.88(s, 3H), 7.08–7.80(m, 4H) | 329, 188 |
| N-(4-pyridyl)-1,2 3,4-tetrahydrobenzo[b]thieno[2,3-c]pyridine-3-carboxamide hydrochloride | 2945, 1660, 1545, 1420, 760 | 2.96–4.26(m, 5H), 6.50–8.07(m, 8H) | 308, 188 |
| N-phenyl-1,2,3,4-tetrahydrobenzo-[b]thieno[2,3-c]pyridine-3-carboxamide hydrochloride | 1680, 1600, 1440, 750 | 2.38–4.05(m, 5H), 6.98–8.05(m, 9H), | 309, 188 |
| N-(1-pyrrolinyl)-1,2,3,4-tetrahydrobenzo[b]thieno[2,3-c]-pyridine-3-carboxamide hydrochloride | 2950, 1670, 1440, 755 | 2.31–4.01(m, 5H), 7.01–8.00(m, 4H) | 296, 188 |

TABLE 27

| Final compound | IR ($V_{max}$, cm$^{-1}$) | NMR (δ, CD$_3$OD) | Mass (m/z) |
|---|---|---|---|
| N-{4-(1,2,4-triazolyl)}-1,2,3,4-tetrahydrobenzo[b]thieno[2,3-c]-pyridine-3-carboxamide | 2940, 1660, 1430, 750 | 2.29–4.19(m, 5H), 7.00–7.98(m, 2H), 8.51(s, 2H) | 298, 188 |

TABLE 27-continued

| Final compound | IR ($V_{max}$, cm$^{-1}$) | NMR ($\delta$, CD$_3$OD) | Mass (m/z) |
|---|---|---|---|
| dihydrochloride | | | |
| N-cyclooctyl-1,2,3,4-tetrahydro-benzo[b]thieno[2,3-c]pyridine-3-carboxamide hydrochloride | 2950, 1660, 1450, 760 | 1.13–2.00(m, 15H), 2.43–4.30(m, 5H), 7.26–8.10(m, 4H) | 344, 188 |
| N-(4-piperidinyl)methyl-1,2,3,4-tetrahydrobenzo[b]thieno[2,3-c]-pyridine-3-carboxamide dihydrochloride | 3225, 1660, 1430, 755 | 1.03–3.97(m, 16H), 7.23–8.07(m, 4H) | 330, 188 |
| N-cyclohexylmethyl-1,2,3,4-tetra-hydrobenzo[b]thieno[2,3-c]-pyridine-3-carboxamide hydrochloride | 2900, 1660, 1540, 1420, 750 | 0.50–2.00(m, 11H), 2.37–4.17(m, 7H), 6.67–7.83(m, 4H) | 329, 188 |
| N-(3-pentyl)-1,2,3,4-tetrahydro-benzo[b]thieno[2,3-c]pyridine-3-carboxamide hydrochloride | 3200, 1660, 1545, 1430, 745 | 0.63–1.87(m, 11H), 2.64–4.37(m, 5H), 7.20–8.00(m, 4H) | 303, 188 |

TABLE 28

| Final compound | IR ($V_{max}$, cm$^{-1}$) | NMR ($\delta$, CD$_3$OD) | Mass (m/z) |
|---|---|---|---|
| N-diethyl-1,2,3,4-tetrahydro-benzo[b]thieno[2,3-c]pyridine-3-carboxamide hydrochloride | 2975, 1640, 1440, 760 | 1.47(t, J=6Hz, 6H), 2.47–3.99(m, 9H), 7.16–8.00(m, 4H) | 289, 188 |
| N-(1-adamantyl)-1,2,3,4-tetra-hydrobenzo[b]thieno[2,3-c]-pyridine-3-carboxamide hydrochloride | 2900, 1655, 1560, 1440, 760 | 1.57–2.19(m, 15H), 3.00–4.02(m, 5H), 7.24–8.00(m, 4H) | 367, 188 |
| N-(3-quinuclidinyl)-1,2,3,4-tetra-hydrobenzo[b]thieno[2,3-c]-pyridine-3-carboxamide dihydrochloride | 2940, 1670, 1430, 760 | 1.60–4.12(m, 18H), 7.24–7.98(m, 4H) | 340, 188 |
| N-(exo-2-norbornyl)-1,2,3,4-tetrahydrobenzo[b]thieno[2,3-c]-pyridine-3-carboxamide hydrochloride | 3240, 2960, 1680, 1540, 1430, 760 | 0.87–4.67(m, 16H), 7.23–8.00(m, 4H) | 325, 188 |
| 1-(3-chlorophenyl)-4-{3-(1,2,3,4-tetrahydrobenzo[b]thieno[2,3-c]-pyridine)-3-carbonyl}piperazine dihydrochloride | 3340, 2940, 1660, 1540, 1430, 750 | 2.50–4.12(m, 13H), 7.50–8.33(m, 9H) | 412, 188 |

TABLE 29

| Final compound | IR ($V_{max}$, cm$^{-1}$) | NMR ($\delta$, CD$_3$OD) | Mass (m/z) |
|---|---|---|---|
| N-piperonyl-1,2,3,4-tetrahydro-benzo[b]thieno[2,3-c]pyridine-3-carboxamide hydrochloride | 3250, 2900, 1685, 1435, 760 | 2.33–4.12(m, 5H), 5.93(s, 2H), 6.77–8.07(m, 9H) | 367, 188 |
| N-(2-methoxybenzyl)-1,2,3,4-tetra-hydrobenzo[b]thieno[2,3-c]-pyridine-3-carboxamide hydrochloride | 3275, 2900, 1680, 1440, 760 | 2.29–4.37(m, 5H), 3.65–4.11(m, 5H), 6.55–8.19(m, 8H) | 353, 188 |
| N-(3-methoxybenzyl)-1,2,3,4-tetra-hydrobenzo[b]thieno[2,3-c]-pyridine-3-carboxamide hydrochloride | 3260, 2985, 1680, 1450, 760 | 2.30–4.31(m, 5H), 3.69–4.15(m, 5H), 6.59–8.20(m, 8H) | 353, 188 |
| N-(4-methoxybenzyl)-1,2,3,4-tetra-hydrobenzo[b]thieno[2,3-c]-pyridine-3-carboxamide hydrochloride | 3270, 2900, 1685, 1450, 760 | 2.25–4.21(m, 5H), 3.66–4.16(m, 5H), 6.57–8.10(m, 8H) | 353, 188 |
| N-(2,3-dimethoxybenzyl)-1,2,3,4-tetrahydrobenzo[b]thieno[2,3-c]-pyridine-3-carboxamide hydrochloride | 3250, 2910, 1680, 1440, 770 | 2.27–4.33(m, 5H), 3.71–4.02(m, 8H), 6.49–8.20(m, 7H) | 383, 188 |

TABLE 30

| Final compound | IR ($V_{max}$, cm$^{-1}$) | NMR ($\delta$, CD$_3$OD) | Mass (m/z) |
|---|---|---|---|
| N-(2,4-dimethoxybenzyl)-1,2,3,4-tetrahydrobenzo[b]thieno[2,3-c]-pyridine-3-carboxamide hydrochloride | 3240, 2900, 1685, 1450, 760 | 2.25–4.29(m, 5H), 3.69–4.05(m, 8H), 6.51–8.19(m, 7H) | 383, 188 |

TABLE 30-continued

| Final compound | IR (V$_{max}$, cm$^{-1}$) | NMR (δ, CD$_3$OD) | Mass (m/z) |
|---|---|---|---|
| N-(3,4-dimethoxybenzyl)-1,2,3,4-tetrahydrobenzo[b]thieno[2,3-c]-pyridine-3-carboxamide hydrochloride | 3240, 2900, 1680, 1440, 770 | 2.21–4.29(m, 5H), 3.70–4.05(m, 8H), 6.50–8.21(m, 7H) | 383, 188 |
| N-(3,5-dimethoxybenzyl)-1,2,3,4-tetrahydrobenzo[b]thieno[2,3-c]-pyridine-3-carboxamide hydrochloride | 3250, 2900, 1685, 1435, 760 | 2.20–4.25(m, 5H), 3.69–4.05(m, 8H), 6.52–8.19(m, 7H) | 383, 188 |
| N-(2,4,6-trimethoxybenzyl)-1,2,3,4-tetrahydrobenzo[b]thieno[2,3-c]-pyridine-3-carboxamide hydrochloride | 3200, 2920, 1685, 1450, 770 | 2.20–4.31(m, 5H), 3.80–4.02(m, 11H), 6.57–8.20(m, 6H) | 413, 188 |

TABLE 31

| Final compound | IR (V$_{max}$, cm$^{-1}$) | NMR (δ, CD$_3$OD) | Mass (m/z) |
|---|---|---|---|
| N-(3,4,5-trimethoxybenzyl)-1,2,3,4-tetrahydrobenzo[b]thieno[2,3-c]-pyridine-3-carboxamide hydrochloride | 3250, 2900, 1680, 1450, 770 | 2.19–4.29(m, 5H), 3.81–4.04(m, 11H), 6.60–8.15(m, 6H) | 413, 188 |
| N-(α-methylbenzyl)-1,2,3,4-tetra-hydrobenzo[b]thieno[2,3-c]-pyridine-3-carboxamide hydrochloride | 3300, 2930, 1680, 1540, 1420, 777 | 1.49(d, 3H, J=6Hz), 2.41–4.09(m, 5H), 4.00(t, 1H, J=6Hz), 6.88–8.02(m, 9H) | 334, 188 |
| N-(4-methylbenzyl)-1,2,3,4-tetra-hydrobenzo[b]thieno[2,3-c]-pyridine-3-carboxamide hydrochloride | 3280, 2950, 1685, 1550, 770 | 2.31(s, 3H), 2.27–4.11(m, 5H), 3.81(s, 2H), 7.00–8.12(m, 8H) | 334, 188 |
| N-[4-(trifluoromethyl)benzyl]-1,2,3,4,-tetrahydrobenzo[b]thieno-[2,3-c]pyridine-3-carboxamide hydrochloride | 3250, 2930, 1680, 1540, 780 | 2.43–4.22(m, 5H), 3.79(s, 2H), 7.01–8.09(m, 8H) | 388, 188 |
| N-[4-(isopropyl)benzyl]-1,2,3,4-tetrahydrobenzo[b]thieno[2,3-c]-pyridine-3-carboxamide hydrochloride | 3200, 2920, 1685, 1550, 770 | 0.98–4.13(m, 12H), 3.75(s, 2H), 6.98–8.10(m, 8H) | 364, 188 |

TABLE 32

| Final compound | IR (V$_{max}$, cm$^{-1}$) | NMR (δ, CD$_3$OD) | Mass (m/z) |
|---|---|---|---|
| N-[4-(tert-butyl)benzyl]-1,2,3,4-tetrahydrobenzo[b]thieno[2,3-c]-pyridine-3-carboxamide hydrochloride | 3250, 2940, 1680, 1540, 780 | 1.32(s, 9H), 2.42–4.20(m, 5H), 3.75(s, 2H), 7.00–8.10(m, 8H) | 378, 188 |
| N-[4-(isopropyl)phenyl]-1,2,3,4-tetrahydrobenzo[b]thieno[2,3-c]-pyridine-3-carboxamide hydrochloride | 3250, 2930, 1685, 1550, 770, | 0.99–4.17(m, 12H), 7.02–7.99(m, 8H) | 350, 188 |
| N-[4-(tert-butyl)phenyl]-1,2,3,4-tetrahydrobenzo[b]thieno[2,3-c]-pyridine-3-carboxamide hydrochloride | 3230, 2940, 1680, 1540, 780 | 1.30(s, 9H), 2.41–4.21(m, 5H), 7.01–8.09(m, 8H) | 364, 188 |
| N-[trans-2-(phenylcyclopropyl)]-1,2,3,4-tetrahydrobenzo[b]thieno-[2,3-c]pyridine-3-carboxamide hydrochloride | 3250, 2950, 1670, 1530, 770 | 0.72–4.20(m, 9H), 6.81–8.01(m, 9H) | 348, 188 |

TABLE 33

| Final compound | IR (V$_{max}$, cm$^{-1}$) | NMR (δ, CD$_3$OD) | Mass (m/z) |
|---|---|---|---|
| N-ethynylcyclohexyl-1,2,3,4-tetra-hydrobenzo[b]thieno[2,3-c]-pyridine-3-carboxamide hydrochloride | 3250, 2940, 1660, 1540, 780 | 0.90–4.20(m, 15H), 2.38(s, 1H), 6.99–7.98(m, 4H) | 348, 188 |
| N-cyclononyl-1,2,3,4-tetrahydro-benzo[b]thieno[2,3-c]pyridine-3-carboxamide hydrochloride | 2975, 1645, 1560, 1440, 760 | 1.37–4.23(m, 22H), 6.99–7.83(m, 4H) | 355, 188 |
| N-cyclodecanyl-1,2,3,4-tetrahydro-benzo[b]thieno[2,3-c]pyridine-3- | 3230, 1640, 1560, 1450, 770 | 1.20–4.25(m, 22H), 7.01–8.01(m, 4H) | 369, 188 |

TABLE 33-continued

| Final compound | IR (V$_{max}$, cm$^{-1}$) | NMR (δ, CD$_3$OD) | Mass (m/z) |
|---|---|---|---|
| carboxamide hydrochloride | | | |
| N-(2,3-dimethylcyclohexyl)-1,2,3,4-tetrahydrobenzo[b]thieno[2,3-c]-pyridine-3-carboxamide hydrochloride | 3250, 1645, 1570, 1440, 770 | 0.50–4.18(m, 19H), 7.02–7.99(m, 9H) | 341, 188 |
| N-(tert-butyl)-1,2,3,4-tetrahydrobenzo[b]thieno[2,3-c]pyridine-3-carboxamide hydrochloride | 3240, 2950, 1640, 1560, 780 | 1.12(s, 9H), 1.18–4.22(m, 5H), 7.00–7.91(m, 4H) | 287, 188 |

TABLE 34

| Final compound | IR (v$_{max}$, cm$^{-1}$) | NMR (δ, CD$_3$OD) | Mass (m/z) |
|---|---|---|---|
| N-(isoamyl)-1,2,3,4-tetrahydrobenzo[b]thieno[2,3-c]pyridine-3-carboxamide hydrochloride | 3230, 2940, 1645, 1550, 770 | 0.59–4.25 (m, 16H), 6.89–7.89 (m, 4H) | 329, 188 |
| N-[(−)-cis-myrtanyl]-1,2,3,4-tetrahydrobenzo[b]thieno[2,3-c]-pyridine-3-carboxamide hydrochloride | 3250, 2950, 1645, 1540, 780 | 0.80–4.21 (m, 22H), 6.89–7.91 (m, 4H) | 367, 188 |
| N-(endo-2-norbonyl)-1,2,3,4-tetrahydrobenzo[b]thieno[2,3-c]-pyridine-3-carboxamide hydrochloride | 3250, 2950, 1670, 1545, 1425, 755 | 0.90–4.18 (m, 16H), 7.11–8.02 (m, 4H) | 325, 188 |
| N-cyclododecyl-1,2,3,4-tetrahydrobenzo[b]thieno[2,3-c]pyridine-3-carboxamide hydrochloride | 3240, 2940, 1660, 1540, 1415, 760 | 1.10–4.23 (m, 28H), 7.01–7.99 (m, 4H) | 398, 188 |
| N-(isobutyl)-1,2,3,4-tetrahydrobenzo[b]thieno[2,3-c]pyridine-3-carboxamide hydrochloride | 3230, 2950, 1670, 1540, 1420, 770 | 0.72–1.98 (m, 6H), 2.43–3.68 (m, 8H), 7.10–8.02 (m, 4H) | 287, 188 |

TABLE 35

| Final compound | IR (v$_{max}$, cm$^{-1}$) | NMR (δ, CD$_3$OD) | Mass (m/z) |
|---|---|---|---|
| N-diisopropyl-1,2,3,4-tetrahydrobenzo[b]thieno[2,3-c]pyridine-3-carboxamide hydrochloride | 3240, 2940, 1665, 1540, 1415, 750 | 1.04(d, J=6H, 12H), 2.31–4.01 (m, 7H), 7.01–8.01 (m, 4H) | 315, 188 |
| N-(1,3-dimethylbutyl)-1,2,3,4-tetrahydrobenzo[b]thieno[2,3-c]pyridine-3-carboxamide hydrochloride | 3300, 2950, 1670, 1540, 1420, 740 | 0.74–2.05 (m, 13H), 2.29–3.78 (m, 5H), 7.10–7.98 (m, 4H) | 315, 188 |
| N-(2-heptyl)-1,2,3,4-tetrahydrobenzo[b]thieno[2,3-c]pyridine-3-carboxamide hydrochloride | 3250, 2940, 1660, 1540, 1430, 760 | 0.65–1.82 (m, 15H), 2.28–3.70 (m, 4H), 6.98–7.91 (m, 4H) | 329, 188 |
| N-(4-heptyl)-1,2,3,4-tetrahydrobenzo[b]thieno[2,3-c]pyridine-3-carboxamide hydrochloride | 3260, 2945, 1670, 1545, 1440, 770 | 0.59–1.78 (m, 15H), 2.40–3.68 (m, 5H), 7.11–7.99 (m, 4H) | 329, 188 |
| N-(2-octyl)-1,2,3,4-tetrahydrobenzo[b]thieno[2,3-c]pyridine-3-carboxamide hydrochloride | 3240, 2945, 1665, 1540, 1435, 770 | 0.65–1.75 (m, 17H), 2.37–3.57 (m, 5H), 7.13–7.99 (m, 4H) | 343, 188 |

TABLE 36

| Final compound | IR (v$_{max}$, cm$^{-1}$) | NMR (δ, CD$_3$OD) | Mass (m/z) |
|---|---|---|---|
| N-(sec-butyl)-1,2,3,4-tetrahydrobenzo[b]thieno[2,3-c]pyridine-3-carboxamide hydrochloride | 3245, 2940, 1670, 1540, 1435, 770 | 0.70–1.60 (m, 8H), 2.35–3.98 (m, 5H), 7.20–8.09 (m, 4H) | 287, 188 |
| N-(2-pentyl)-1,2,3,4-tetrahydrobenzo[b]thieno[2,3-c]pyridine-3-carboxamide hydrochloride | 3200, 2945, 1660, 1545, 1425, 750 | 0.65–1.82 (m, 11H), 2.55–3.88 (m, 5H), 7.27–8.10 (m, 4H) | 303, 188 |
| N-(tert-amyl)-1,2,3,4-tetrahydrobenzo[b]thieno[2,3-c]pyridine-3-carboxamide hydrochloride | 3225, 2940, 1665, 1540, 1435, 760 | 0.70–1.55 (m, 11H), 2.39–3.61 (m, 5H), 7.13–7.99 (m, 4H) | 301, 188 |
| N-(1,2-dimethylpropyl)-1,2,3,4-tetrahydrobenzo[b]thieno[2,3-c]pyridine-3-carboxamide hydrochloride | 3220, 2945, 1670, 1535, 1430, 750 | 0.68–1.59 (m, 11H), 2.35–3.98 (m, 5H), 7.20–8.09 (m, 4H) | 301, 188 |
| N-(1,5-dimethylhexyl)-1,2,3,4-tetrahydrobenzo[b]thieno[2,3-c]-pyridine)-3-carboxamide hydrochloride | 3250, 2940, 1660, 1540, 1440, 770 | 0.75–2.00 (m, 17H), 2.39–3.61 (m, 5H), 7.13–7.99 (m, 4H) | 343, 188 |

TABLE 37

| Final compound | IR (v$_{max}$, cm$^{-1}$) | NMR (δ, CD$_3$OD) | Mass (m/z) |
|---|---|---|---|
| N-(2-ethylhexyl)-1,2,3,4-tetrahydrobenzo[b]thieno[2,3-c]-pyridine-3-carboxamide hydrochloride | 3245, 2945, 1660, 1545, 1430, 760 | 0.61–1.98 (m, 17H), 2.35–3.98 (m, 5H), 7.20–8.09 (m, 4H) | 343, 188 |
| N-(1,1,3,3-tetramethylbutyl)-1,2,3,4-tetrahydrobenzo[b]thieno[2,3-c]-pyridine-3-carboxamide hydrochloride | 3250, 2945, 1665, 1545, 1430, 760 | 1.02 (s, 15H), 1.12 (s, 2H), 2.48–3.59 (m, 5H), | 343, 188 |

TABLE 37-continued

| Final compound | IR ($v_{max}$, cm$^{-1}$) | NMR (δ, CD$_3$OD) | Mass (m/z) |
|---|---|---|---|
| N-octyl-1,2,3,4-tetrahydro-benzo[b]thieno[2,3-c]pyridine-3-carboxamide hydrochloride | 3260, 2940, 1660, 1540, 1425, 770 | 7.21–8.01 (m, 4H) 0.59–1.81 (m, 17H), 2.49–3.50 (m, 5H), 7.27–8.10 (m, 4H) | 343, 188 |
| N-[(S)-(−)-2-methylbutyl]-1,2,3,4-tetrahydrobenzo[b][2,3-c]-pyridine-3-carboxamide hydrocloride | 3245, 2950, 1665, 1540, 1420, 760 | 0.68–1.82 (m, 11), 2.39–3.61 (m, 5H), 7.13–7.99 (m, 4H) | 301, 188 |
| N-(3,3-dimethylpropyl)-1,2,3,4-tetrahydrobenzo[b]thieno[2,3,-c]pyridine-3-carboxamide hydrochloride | 3245, 2950, 1670, 1540, 1425, 770 | 0.71–2.00 (m, 13H), 2.35–3.98 (m, 5H), 7.20–8.09 (m, 4H) | 301, 188 |

TABLE 38

| Final compound | IR ($v_{max}$, cm$^{-1}$) | NMR (δ, CD$_3$OD) | Mass (m/z) |
|---|---|---|---|
| cyclohexyl 1,2,3,4-tetrahydrobenzo[b]thieno[2,3-c]pyridine-3-carboxylate hydrochloride | 1720, 1480, 1320, 760 | 0.99–2.12 (m, 11H), 2.49–3.50 (m, 5H), 7.27–8.10 (m, 4H) | 316, 234, 188 |
| cyclopentyl 1,2,3,4-tetrahydrobenzo[b]thieno[2,3-c]pyridine-3-carboxylate hydrochloride | 1720, 1470, 1340, 770 | 0.98–2.13 (m, 9H), 2.39–3.61 (m, 5H), 7.13–7.99 (m, 4H) | 302, 188 |
| cycloheptyl 1,2,3,4-tetrahydrobenzo[b]thieno[2,3-c]pyridine-3-carboxylate hydrocloride | 1725, 1480, 1350, 770 | 0.96–2.22 (m, 13H), 2.35–3.98 (m, 5H), 7.20–8.09 (m, 4H) | 330, 188 |
| cyclooctyl 1,2,3,4-tetrahydrobenzo[b]thieno[2,3-c]pyridine-3-carboxylate hydrochloride | 1720, 1470, 1340, 780 | 0.96–2.22 (m, 15H), 2.32–3.87 (m, 5H), 7.17–8.05 (m, 4H) | 344, 188 |
| cyclohexylmethyl 1,2,3,4-tetrahydrobenzo[b]thieno[2,3-c]-pyridine-3-carboxylate hydrochloride | 1715, 1480, 1340, 775 | 0.89–2.29 (m, 18H), 7.08–8.05 (m, 4H) | 330, 188 |

TABLE 39

| Final compound | IR ($v_{max}$, cm$^{-1}$) | NMR (δ, CD$_3$OD) | Mass (m/z) |
|---|---|---|---|
| N-cyclohexyl-6-hydroxy-1,2,3,4-tetrahydrobenzo[b]thieno[2,3-c]-pyridine-3-carboxamide hydrochloride | 3480, 1645, 1475, 1345, 770 | 0.80–2.29 (m, 11H), 2.95–4.35 (m, 5H), 7.15–8.35 (m, 3H) | 330, 188 |

EXAMPLE 5

N-cyclohexyl-1,2,3,4-tetrahydrobenzo[b]thieno[2,3-c]pyridine-3-carboxamide-9-oxide was synthesized in accordance with the following method.

30 g of N-cyclohexyl-1,2,3,4-tetrahydrobenzo[b]thieno[2,3-c]pyridine-3-carboxamide methanesulfonate was added to a solution of 300 ml of chloroform and 16.23 g of triethylamine and the resulting mixture was stirred at room temperature for 1 hour. Then 41.5 ml of benzyloxycarbonyl chloride was added thereto under ice-cooling and the resulting mixture was stirred at room temperature for 3 hours. The reaction mixture was washed with 20 ml of water thrice and dried over magnesium sulfate. The reaction mixture was distilled under reduced pressure and the residue was separated by silica gel column chromatography (solvent: chloroform). Thus 23.6 g of N-cyclohexyl-2-(benzyloxycarbonyl)-1,2,3,4-tetrahydrobenzo[b]thieno[2,3-c]pyridine-3-carboxamide (yield: 87%) was obtained. The NMR data of this product were as follows. It was confirmed that this product is N-cyclohexyl-2-(benzyloxycarbonyl)-1,2,3,4-tetrahydrobenzo[b]thieno[2,3-c]pyridine-3-carboxamide.

NMR (δ, CDCl$_3$): 0.63–2.10 (m, 11H), 2.90–5.10 (m, 5H), 5.20 (s,2H), 7.00–7.90 (m, 9H).

200 ml of acetic acid was introduced into a 2,000 ml-volume eggplant type flask and 100 mg of selenium dioxide was added thereto. Under stirring at room temperature, 7.6 ml of a 31% aqueous solution of hydrogen peroxide was added thereto. Further, 11.91 g of N-cyclohexyl-2-(benzyloxycarbonyl)-1,2,3,4-tetrahydrobenzo[b]thieno[2,3-c]pyridine-3-carboxamide dissolved in 600 ml of acetic acid was added thereto and the resulting mixture was stirred at room temperature. Four hours later, 3.4 ml of a 31% aqueous solution of hydrogen peroxide was further added thereto and the mixture was stirred overnight. Then the reaction mixture was poured onto ground ice and adjusted to about pH 6 with 6N to 1N NaOH. Then it was extracted with 500 ml of chloroform twice, washed with water, dried over magnesium sulfate and distilled under reduced pressure. The residue was purified by silica gel column (solvent: chloroform) to give thereby 15.73 g of N-cyclohexyl-2-(benzyloxycarbonyl)-1,2,3,4-tetrahydrobenzo[b]thieno[2,3-c]pyridine-3-carboxamide-9-oxide (yield: 51.4 g).

Mass (m/z): 465, 449, 405, 303, 188.

To a 1,000 ml-volume eggplant type flask containing 15.7 g of N-cyclohexyl-1,2,3,4-tetrahydrobenzo[b]thieno[2,3-c]pyridine-3-carboxamide-9-oxide, 100 ml each of 1M trifluoromethanesulfonic acid and a 1M solution of anisole in methanesulfonic acid were added and the mixture was stirred at room temperature for 1 hour. After the completion of the reaction, the reaction mixture was poured into ice water and adjusted to about pH 7 with 6N to 1N NaOH. Then it was extracted with 500 ml of chloroform twice, washed with water, dried over magnesium sulfate and distilled under reduced pressure. The residue was separated and purified by silica gel column (solvent: chloroform) to give thereby 154 mg of N-cyclohexyl-1,2,3,4-tetrahydrobenzo[b]thieno[2,3-c]pyridine-3-carboxamide-9-oxide (yield: 1.4%) in the form of a white solid.

IR ($v_{max}$, cm$^{-1}$): 3280, 2930, 1645, 1030, 760.

NMR (δ, CDCl$_3$): 0.75–2.25 (m, 11H), 2.62–4.08 (m, 5H), 6.72–8.00 (m, 4H).

Mass (m/z): 331, 315, 313, 188.

EXAMPLE 6

The procedure of Example 5 was repeated except for replacing 30 g of the N-cyclohexyl-1,2,3,4-tetrahydrobenzo[b]thieno[2,3-c]pyridine-3-carboxamide methanesulfonate employed in Example 5 with 31.2 g of N-cyclohexyl-6-hydroxy-1,2,3,4-tetrahydrobenzo[b]thieno[2,3-c]pyridine-3-carboxamide methanesulfonate and 32.3 g of N-(4-hydroxycyclohexyl)-6 -hydroxy-1,2,3,4-tetrahydrobenzo[b]thieno[2,3-c]pyridine-3-carboxamide methanesulfonate to give thereby N-cyclohexyl-6-hydroxy-1,2,3,4-tetrahydrobenzo[b]thieno[2,3-c]pyridine-3-carboxamide-9-oxide and N-(4-hydroxycyclohexyl)-6-hydroxy-1,2,3,4-tetrahydrobenzo[b]thieno[2,3-c]pyridine-3-carboxamide-9-oxide, respectively.

Table 40 shows the results while Table 41 shows the analytical data.

TABLE 40

| Reactant | Reactant | Reaction temperature | Reaction time | Final yield | Final product |
|---|---|---|---|---|---|
| N-cyclohexyl-6-hydroxy-1,2,3,4-tetrahydrobenzo[b]-thieno[2,3-c]-pyridinecarboxamide methanesulfonate | | | | | |
| 31.2 g | benzyloxycarbonyl chloride 41.5 ml | room temp. | 1 day | 241 mg (2.1%) | N-cyclohexyl-6-hydroxy-1,2,3,4-tetrahydrobenzo[b]thieno[2,3-c]pyridine-3-carboxamide-9-oxide |
| N-(4-hydroxycyclohexyl)-6-hydroxy-1,2,3,4-tetrahydrobenzo-[b]thieno[2,3-c]-pyridine-carbamide methanesulfonate | | | | | |
| 32.3 g | benzyloxycarbonyl chloride 41.5 ml | room temp. | 1 day | 119 mg (1.1%) | N-(4-hydroxycyclohexyl)-6-hydroxy-1,2,3,4-tetrahydrobenzo[b]-thieno[2,3-c]pyridine-3-carboxamide-9-oxide |

TABLE 41

| Final compound | IR ($v_{max}$, cm$^{-1}$) | NMR ($\delta$, CD$_3$OD) | Mass (m/z) |
|---|---|---|---|
| N-cyclohexyl-6-hydroxy-1,2,3,4-tetrahydrobenzo[b]-thieno[2,3-c]-pyridine-3-carboxamide-9-oxide | 3345, 2935, 1650, 1030, 755 | 0.98–2.22 (m, 10H), 2.94–4.18 (m, 5H), 6.78–7.95 (m, 3H) | 347, 331, 315, 188 |
| N-(4-hydroxycyclohexyl)-6-hydroxy-1,2,3,4-tetrahydrobenzo[b]thieno-[2,3-c]pyridine-3-carboxamide-9-oxide | 3350, 2925, 1640, 1040, 755 | 0.99–2.12 (m, 10H), 2.70–4.10 (m, 5H), 6.85–7.98 (m, 3H) | 363, 347, 331, 188 |

EXAMPLE 7

N-cyclohexyl-1,2,3,4-tetrahydrobenzo[b]thieno[2,3-c]pyridine-3-carboxamide-9-dioxide hydrochloride was synthesized in accordance with the following method.

4.02 g of N-cyclohexyl-2-(benzyloxycarbonyl)-1,2,3,4-tetrahydrobenzo[b]thieno[2,3-c]pyridine-3-carboxamide was added to 40 ml of acetic acid at room temperature. Further, 1.5 ml of a 31% aqueous solution of hydrogen peroxide was added thereto and the mixture was refluxed for 30 minutes. Under ice-cooling, the pH value of the reaction mixture was adjusted to 7 with a saturated solution of sodium hydrogencarbonate. Then it was extracted with 100 ml of chloroform twice. The chloroform layer was dried over magnesium sulfate and distilled under reduced pressure. The residue was separated by silica gel column chromatography (solvent: chloroform). Thus, 2.22 g of N-cyclohexyl-2-(benzyloxycarbonyl)-1,2,3,4-tetrahydrobenzo[b]thieno[2,3-c]pyridine-3-carboxamide-9-dioxide (yield: 52%) was obtained. The mass spectrum data of this product were as follows. It was confirmed that this product is N-cyclohexyl-2-(benzyloxycarbonyl)-1,2,3,4-tetrahydrobenzo[b]thieno[2,3-c]pyridine-3-carboxamide-9-dioxide.

Mass (m/z): 482, 465, 449, 405, 186.

8.0 g of N-cyclohexyl-2-(benzyloxycarbonyl)-1,2,3,4-tetrahydrobenzo[b]thieno[2,3-c]pyridine-3-carboxamide-9-dioxide was added to 20 ml of acetic acid. Further, 30 ml of 25% hydrogen bromide/acetic acid was added thereto and the mixture was stirred at room temperature for 1 hour. The white crystals thus precipitated were collected by filtration. Thus, 5.6 g of N-cyclohexyl-1,2,3,4-tetrahydrobenzo[b]thieno[2,3-c]pyridine-3-carboxamide-9-dioxide hydrobromide was obtained (yield: 79.5%).

3.08 g of N-cyclohexyl-1,2,3,4-tetrahydrobenzo[b]thieno[2,3-c]pyridine-3-carboxamide-9-dioxide hydrobromide was dissolved in 100 ml of water and 20 ml of a 1N solution of sodium hydroxide was further added thereto. After extracting with 50 ml of chloroform twice, the chloroform layer was distilled under reduced pressure. To the residue, 3 ml of 10% hydrochloric acid/methanol was added and the mixture was stirred at room temperature for 2 hours. The white crystals thus precipitated were collected by filtration and, thus, 1.4 g of N-cyclohexyl-1,2,3,4-tetrahydrobenzo[b]thieno[2,3-c]pyridine-3-carboxamide-9-dioxide hydrochloride was obtained (yield: 50.7%). The NMR, IR and mass spectrum data of this product were as follows. It was confirmed that this product is N-cyclohexyl-1,2,3,4-tetrahydrobenzo[b]thieno[2,3-c]pyridine-3-carboxamide-9-dioxide hydrochloride.

IR ($v_{max}$, cm$^{-1}$): 3250, 2950, 1680, 1318, 1160, 780.

NMR (δ, CDCl$_3$): 1.00–2.10 (m, 11H), 1.47–4.30 (m, 6H), 7.02–8.10 (m, 4H).

Mass (m/z): 347, 281, 220, 156.

EFFECTS OF THE INVENTION

The compound according to the present invention shows specific antianxiety and learning-improvement effects as described below.

By using male Wistar rats aged 6 weeks, the antianxiety and learning-improvement effects of the compounds of the present invention were examined by the water lick conflict test with reference to Vogel J. R., Beer B. and Clody D. E., Psychopharmacologia, 1–7, 21 (1971).

In this test, rats, which had been forbidden to take water, were made in conflict (anxiety) by subjecting to electric shock every time they took water and thus the effect of a drug thereon was examined.
(Anxiolytic Effect)

Rats, which had been deprived of water for 24 hours prior to the test, were allowed to take water. 4 to 5 hours thereafter, a test compound was administrated to them and, after the treating period, the test was initiated. The frequency of shock means the number of the electric shocks applied within 5 minutes after a rat began to drink water and indicates whether the conflict (anxiety) that the electric shock might occur after drinking water could be suppressed or not. That is to say, an increase in the frequency of shock means that the anxiolytic effect has been enhanced.

Tables 42 to 59 show the values calculated by referring the data of control rats (no drug administration) as to 100 (n=5).

In order to compare with the prior arts, β-carboline-3-ethyl ester (referred to simply as β-CCE) which is a typical example of the compounds disclosed in JP-A-56-43283, 6-chloro-1,2,3,4-tetrahydrobenzothieno[2,3-c]pyridine (referred to simply as C-1) which is a typical example of the compounds disclosed in JP-B-50-2519 (the term "JP-B" as used herein means an "examined Japanese patent publication"), ethyl benzothieno[2,3-c]pyridine-3-carboxylate (referred to simply as A-1) which is a typical example of the compounds disclosed in JP-A-61-236779, ethyl 1,2,3,4-tetrahydrobenzothieno[2,3-c]pyridine-3-carboxylate (referred to simply as A-2) which is a typical example of the compounds disclosed in JP-A-63-096188, hexahydro-1-(benzothieno[2,3-c]pyridine-3-carbonyl)-1H-1,4-diazepine (referred to simply as A-3) which is a typical example of the compounds disclosed in JP-A-63-096189,N-(2-aminoethyl-benzothieno[2,3-c]pyridine-3 -carboxamide (referred to simply as A-4) which is a typical example of the compounds disclosed in JP-A-1-100172, N-ethyl-1,2,3,4-tetrahydrobenzothieno[2,3-c]pyridine-3-carboxamide (referred to simply as A-5) which is a typical example of the compounds disclosed in JP-A-2-149583 and N-cyclohexyl-1,2,3,4-tetrahydrobenzothieno[2,3-c]pyridine-3-carboxamide hydrochloride (referred to simply as A-6) which is a typical example of the compounds disclosed in JP-A-2-149583 are also given in addition to the compounds of the present invention.

Based on these results, it is proved that the compounds of the present invention have anxiolytic effect.

TABLE 42

Anxiolytic effect

| Compound | Dose (mg/kg) | Administration route | Number of shock suffered (Number per 5 minutes) |
| --- | --- | --- | --- |
| Control | | | 100 ± 14.3 |
| β-CCE | 40 | P.O. | 82.0 ± 20.0 |
| C-1 | 40 | P.O. | 104.3 ± 28.6 |
| A-1 | 40 | P.O. | 117.1 ± 25.7 |
| A-2 | 40 | P.O. | 126.5 ± 26.1 |
| A-3 | 40 | P.O. | 123.8 ± 24.4 |
| A-4 | 40 | P.O. | 127.0 ± 23.3 |
| A-5 | 40 | P.O. | 127.1 ± 31.5 |
| A-6 | 40 | P.O. | 389 ± 41** |
| N-(trans-4-hydroxycyclohexyl)-1,2,3,4-tetrahydrobenzo[b]-thieno[2,3-c]pyridine-3-carboxamide hydrochloride | 20 | P.O. | 354 ± 39** |
| N-(cis-4-hydroxycyclohexyl)-1,2,3,4-tetrahydrobenzo[b]-thieno[2,3-c]pyridine-3-carboxamide hydrochloride | 20 | P.O. | 346 ± 35** |

**P < 0.05 (t calibration).

TABLE 43

Anxiolytic effect

| Compound | Dose (mg/kg) | Administration route | Number of shock suffered (Number per 5 minutes) |
| --- | --- | --- | --- |
| (+)-N-(trans-4-hydroxycyclohexyl)-1,2,3,4-tetrahydrobenzo[b]thieno[2,3-c]pyridine-3- | 20 | P.O. | 396 ± 49** |

TABLE 43-continued

Anxiolytic effect

| Compound | Dose (mg/kg) | Administration route | Number of shock suffered (Number per 5 minutes) |
|---|---|---|---|
| carboxamide hydrochloride | | | |
| (+)-N-(cis-4-hydroxycyclohexyl)-1,2,3,4-tetrahydrobenzo-[b]thieno[2,3-c]pyridine-3-carboxamide hydrochloride | 20 | P.O. | 345 ± 54** |
| (−)-N-(trans-4-hydroxycyclo-hexyl)-1,2,3,4-tetrahydrobenzo-[b]thieno[2,3-c]pyridine-3-carboxamide hydrochloride | 20 | P.O. | 355 ± 55** |
| (−)-N-(cis-4-hydroxycyclohexyl)-1,2,3,4-tetrahydrobenzo-[b]thieno[2,3-c]pyridine-3-carboxamide hydrochloride | 20 | P.O. | 336 ± 45** |

**$P < 0.05$ (t calibration).

TABLE 44

Anxiolytic effect

| Compound | Dose (mg/kg) | Administration route | Number of shock suffered (Number per 5 minutes) |
|---|---|---|---|
| N-(2-hydroxycyclohexyl)-1,2,3,4-tetrahydrobenzo[b]thieno[2,3-c]-pyridine-3-carboxamide hydrochloride | 20 | P.O. | 355 ± 39** |
| N-(4-methylcyclohexyl)-1,2,3,4-tetrahydrobenzo[b]thieno[2,3-c]-pyridine-3-carboxamide hydrochloride | 20 | P.O. | 328 ± 31** |
| N-(2-methylcyclohexyl)-1,2,3,4-tetrahydrobenzo[b]thieno[2,3-c]pyridine-3-carboxamide hydrochloride | 20 | P.O. | 347 ± 35** |
| N-(4-tert-butylcyclohexyl)-1,2,3,4-tetrahydrobenzo[b]thieno-[2,3-c]pyridine-3-carboxamide hydrochloride | 20 | P.O. | 346 ± 54** |
| N-(4-aminocyclohexyl)-1,2,3,4-tetrahydrobenzo[b]thieno[2,3-c]-pyridine-3-carboxamide trihydrochloride | 20 | P.O. | 354 ± 55** |

**$P < 0.05$ (t calibration).

TABLE 45

Anxiolytic effect

| Compound | Dose (mg/kg) | Administration route | Number of shock suffered (Number per 5 minutes) |
|---|---|---|---|
| N-piperidino-1,2,3,4-tetrahydro-benzo[b]thieno[2,3-c]pyridine-3-carboxamide dihydrochloride | 20 | P.O. | 337 ± 45** |
| N-{1-(4-methylpiperazinyl)}-1,2,3,4-tetrahydrobenzo[b]thieno-[2,3-c]pyridine-3-carboxamide trihydrochloride | 20 | P.O. | 333 ± 23** |
| N-(2,6-dimethylpyridino)-1,2,3,4-tetrahydrobenzo[b]thieno[2,3-c]pyridine-3-carboxamide dihydrochloride | 20 | P.O. | 327 ± 43** |
| N-(1-pyrrolidinyl)-1,2,3,4-tetra-hydrobenzo[b]thieno[2,3-c]-pyridine-3-carboxamide hydrochloride | 20 | P.O. | 388 ± 54** |

TABLE 45-continued

Anxiolytic effect

| Compound | Dose (mg/kg) | Administration route | Number of shock suffered (Number per 5 minutes) |
|---|---|---|---|
| N-[1-{4-(2-hydroxyethyl)-piperazinyl}]-1,2,3,4-tetrahydrobenzo[b]thieno[2,3-c]pyridine-3-carboxamide trihydrochloride | 20 | P.O. | 339 ± 45** |

**P < 0.05 (t calibration).

TABLE 46

Anxiolytic effect

| Compound | Dose (mg/kg) | Administration route | Number of shock suffered (Number per 5 minutes) |
|---|---|---|---|
| N-{4-(1,2-diethyl-pyrrazolidinyl)}-1,2,3,4-tetrahydrobenzo[b]thieno[2,3-c]-pyridine-3-carboxamide trihydrochloride | 20 | P.O. | 347 ± 45** |
| N-cyclohexyl-N-methyl-1,2,3,4-tetrahydrobenzo[b]thieno[2,3-c]pyridine-3-carboxamide hydrochloride | 20 | P.O. | 360 ± 49** |
| N-(4-pyridyl)-1,2,3,4-tetrahydrobenzo[b]thieno[2,3-c]pyridine-3-carboxamide hydrochloride | 20 | P.O. | 346 ± 54** |
| N-phenyl-1,2,3,4-tetrahydrobenzo[b]thieno[2,3-c]pyridine-3-carboxamide hydrochloride | 20 | P.O. | 356 ± 55** |
| N-(1-pyrrolinyl)-1,2,3,4-tetrahydrobenzo[b]thieno[2,3-c]-pyridine-3-carboxamide hydrochloride | 20 | P.O. | 337 ± 45** |

**P < 0.05 (t calibration).

TABLE 47

Anxiolytic effect

| Compound | Dose (mg/kg) | Administration route | Number of shock suffered (Number per 5 minutes) |
|---|---|---|---|
| N-{4-(1,2,4-triazolyl)}-1,2,3,4-tetrahydrobenzo[b]thieno[2,3-c]-pyridine-3-carboxamide hydrochloride | 20 | P.O. | 335 ± 23** |
| N-cyclooctyl-1,2,3,4-tetrahydrobenzo[b]thieno[2,3-c]pyridine-3-carboxamide hydrochloride | 20 | P.O. | 357 ± 43** |
| N-(4-piperidinyl)methyl-1,2,3,4-tetrahydrobenzo[b]thieno[2,3-c]-pyridine-3-carboxamide dihydrochloride | 20 | P.O. | 358 ± 54** |
| N-cyclohexylmethyl-1,2,3,4-tetrahydrobenzo[b]thieno[2,3-c]-pyridine-3-carboxamide hydrochloride | 20 | P.O. | 338 ± 46** |
| N-(3-pentyl)-1,2,3,4-tetrahydrobenzo[b]thieno[2,3-c]pyridine-3-carboxamide hydrochloride | 20 | P.O. | 348 ± 46** |

**P < 0.05 (t calibration).

TABLE 48

Anxiolytic effect

| Compound | Dose (mg/kg) | Administration route | Number of shock suffered (Number per 5 minutes) |
|---|---|---|---|
| N-diethyl-1,2,3,4-tetrahydro-benzo[b]thieno[2,3-c]pyridine-3-carboxamide hydrochloride | 20 | P.O. | 349 ± 32** |
| N-(1-adamantyl)-1,2,3,4-tetra-hydrobenzo[b]thieno[2,3-c]-pyridine-3-carboxamide hydrochloride | 20 | P.O. | 339 ± 41** |
| N-(3-quinuclidinyl)-1,2,3,4-tetrahydrobenzo[b]thieno[2,3-c]pyridine-3-carboxamide dihydrochloride | 20 | P.O. | 358 ± 46** |
| N-(exo-2-norbonyl)-1,2,3,4-tetra-hydrobenzo[b]thieno[2,3-c]-pyridine-3-carboxamide hydrochloride | 20 | P.O. | 360 ± 54** |
| N-(3-chlorophenyl)-4-{3-(1,2,3,4-tetrahydrobenzo[b]thieno[2,3-c]-pyridine)carbonyl}piperazine dihydrochloride | 20 | P.O. | 339 ± 25** |

**$P < 0.05$ (t calibration).

TABLE 49

Anxiolytic effect

| Compound | Dose (mg/kg) | Administration route | Number of shock suffered (Number per 5 minutes) |
|---|---|---|---|
| N-piperonyl-1,2,3,4-tetrahydro-benzo[b]thieno[2,3-c]pyridine-3-carboxamide hydrochloride | 20 | P.O. | 356 ± 44** |
| N-(2-methoxybenzyl)-1,2,3,4-tetrahydrobenzo[b]thieno[2,3-c]-pyridine-3-carboxamide hydrochloride | 20 | P.O. | 338 ± 54** |
| N-(3-methoxybenzyl)-1,2,3,4-tetrahydrobenzo[b]thieno[2,3-c]-pyridine-3-carboxamide hydrochloride | 20 | P.O. | 349 ± 45** |
| N-(4-methoxybenzyl)-1,2,3,4-tetrahydrobenzo[b]thieno[2,3-c]-pyridine-3-carboxyamide hydrochloride | 20 | P.O. | 355 ± 40** |
| N-(2,3-dimethoxybenzyl)-1,2,3,4-tetrahydrobenzo[b]thieno[2,3-c]-pyridine-3-carboxyamide hydrochloride | 20 | P.O. | 353 ± 41** |

**$P < 0.05$ (t calibration).

TABLE 50

Anxiolytic effect

| Compound | Dose (mg/kg) | Administration route | Number of shock suffered (Number per 5 minutes) |
|---|---|---|---|
| N-(2,4-dimethoxybenzyl)-1,2,3,4-tetrahydrobenzo[b]thieno[2,3-c]-pyridine-3-carboxamide hydrochloride | 20 | P.O. | 337 ± 53** |
| N-(3,4-dimethoxybenzyl)-1,2,3,4-tetrahydrobenzo[b]thieno[2,3-c]-pyridine-3-carboxamide hydrochloride | 20 | P.O. | 358 ± 42** |
| N-(3,5-dimethoxybenzyl)-1,2,3,4-tetrahydrobenzo[b]thieno[2,3-c]-pyridine-3-carboxamide hydrochloride | 20 | P.O. | 355 ± 39** |

TABLE 50-continued

Anxiolytic effect

| Compound | Dose (mg/kg) | Administration route | Number of shock suffered (Number per 5 minutes) |
|---|---|---|---|
| N-(2,4,6-trimethoxybenzyl)-1,2,3,4-tetrahydrobenzo[b]thieno[2,3-c]pyridine-3-carboxamide hydrochloride | 20 | P.O. | 357 ± 45** |
| N-(3,4,5-trimethoxybenzyl)-1,2,3,4-tetrahydrobenzo[b]thieno-[2,3-c]pyridine-3-carboxamide hydrochloride | 20 | P.O. | 349 ± 54** |

**$P < 0.05$ (t calibration).

TABLE 51

Anxiolytic effect

| Compound | Dose (mg/kg) | Administration route | Number of shock suffered (Number per 5 minutes) |
|---|---|---|---|
| N-(α-methylbenzyl)-1,2,3,4-tetrahydrobenzo[b]thieno[2,3-c]-pyridine-3-carboxamide hydrochloride | 20 | P.O. | 339 ± 55** |
| N-(4-methylbenzyl)-1,2,3,4-tetrahydrobenzo[b]thieno[2,3-c]-pyridine-3-carboxamide hydrochloride | 20 | P.O. | 359 ± 41** |
| N-[4-(trifluoromethyl)benzyl]-1,2,3,4-tetrahydrobenzo[b]thieno-[2,3-c]-pyridine-3-carboxamide hydrochloride | 20 | P.O. | 356 ± 39** |
| N-[4-(isopropyl)benzyl]-1,2,3,4-tetrahydrobenzo[b]thieno[2,3-c]-pyridine-3-carboxamide hydrochloride | 20 | P.O. | 348 ± 35** |
| N-[4-(tert-butyl)benzyl]-1,2,3,4-tetrahydrobenzo[b]thieno[2,3-c]-pyridine-3-carboxamide hydrochloride | 20 | P.O. | 359 ± 49** |

**$P < 0.05$ (t calibration).

TABLE 52

Anxiolytic effect

| Compound | Dose (mg/kg) | Administration route | Number of shock suffered (Number per 5 minutes) |
|---|---|---|---|
| N-[4-(isopropyl)phenyl]-1,2,3,4-tetrahydrobenzo[b]thieno[2,3-c]-pyridine-3-carboxamide hydrochloride | 20 | P.O. | 360 ± 54** |
| N-[4-(tert-butyl)phenyl]-1,2,3,4-tetrahydrobenzo[b]thieno[2,3-c]-pyridine-3-carboxamide hydrochloride | 20 | P.O. | 355 ± 57** |
| N-[trans-2-(phenylcyclopropyl)]-1,2,3,4-tetrahydrobenzo[b]-thieno[2,3-c]pyridine-3-carboxamide hydrochloride | 20 | P.O. | 337 ± 45** |
| N-ethynylcyclohexyl-1,2,3,4-tetrahydrobenzo[b]thieno[2,3-c]-pyridine-3-carboxamide hydrochloride | 20 | P.O. | 336 ± 25** |
| N-cyclononyl-1,2,3,4-tetrahydrobenzo[b]thieno[2,3-c]pyridine-3-carboxamide hydrochloride | 20 | P.O. | 326 ± 44** |

**$P < 0.05$ (t calibration).

TABLE 53

| | Anxiolytic effect | | |
|---|---|---|---|
| Compound | Dose (mg/kg) | Administration route | Number of shock suffered (Number per 5 minutes) |
| N-cyclodecanyl-1,2,3,4-tetra-hydrobenzo[b]thieno[2,3-c]-pyridine-3-carboxamide hydrochloride | 20 | P.O. | 358 ± 54** |
| N-(2,3-dimethylcyclohexyl)-1,2,3,4-tetrahydrobenzo[b]thieno-[2,3-c]pyridine-3-carboxamide hydrochloride | 20 | P.O. | 339 ± 45** |
| N-(tert-butyl)-1,2,3,4-tetra-hydrobenzo[b]thieno[2,3-c]-pyridine-3-carboxamide hydrochloride | 20 | P.O. | 358 ± 45** |
| N-(isoamyl)-1,2,3,4-tetrahydro-benzo[b]thieno[2,3-c]pyridine-3-carboxamide hydrochloride | 20 | P.O. | 356 ± 31** |
| N-[(−)cis-myrtanyl]-1,2,3,4-tetrahydrobenzo[b]thieno[2,3-c]-pyridine-3-carboxamide hydrochloride | 20 | P.O. | 328 ± 33** |

**$P < 0.05$ (t calibration).

TABLE 54

| | Anxiolytic effect | | |
|---|---|---|---|
| Compound | Dose (mg/kg) | Administration route | Number of shock suffered (Number per 5 minutes) |
| N-(endo-2-norbonyl)-1,2,3,4-tetrahydrobenzo[b]thieno[2,3-c]-pyridine-3-carboxamide hydrochloride | 20 | P.O. | 349 ± 46** |
| N-cyclododecyl-1,2,3,4-tetra-hydrobenzo[b]thieno[2,3-c]-pyridine-3-carboxamide hydrochloride | 20 | P.O. | 351 ± 29** |
| N-(isobutyl)-1,2,3,4-tetrahydro-benzo[b]thieno[2,3-c]pyridine-3-carboxamide hydrochloride | 20 | P.O. | 334 ± 32** |
| N-diisopropyl-1,2,3,4-tetrahydro-benzo[b]thieno[2,3-c]pyridine-3-carboxamide hydrochloride | 20 | P.O. | 352 ± 36** |
| N-(1,3-dimethylbutyl)-1,2,3,4-tetrahydrobenzo[b]thieno[2,3-c]-pyridine-3-carboxamide hydrochloride | 20 | P.O. | 345 ± 39** |

**$P < 0.05$ (t calibration).

TABLE 55

| | Anxiolytic effect | | |
|---|---|---|---|
| Compound | Dose (mg/kg) | Administration route | Number of shock suffered (Number per 5 minutes) |
| N-(2-heptyl)-1,2,3,4-tetrahydro-benzo[b]thieno[2,3-c]pyridine-3-carboxamide hydrochloride | 20 | P.O. | 329 ± 35** |
| N-(4-heptyl)-1,2,3,4-tetrahydro-benzo[b]thieno[2,3-c]pyridine-3-carboxamide hydrochloride | 20 | P.O. | 356 ± 49** |
| N-(2-octyl)-1,2,3,4-tetrahydro-benzo[b]thieno[2,3-c]pyridine-3-carboxamide hydrochloride | 20 | P.O. | 345 ± 54** |
| N-(sec-butyl)-1,2,3,4-tetrahydro-benzo[b]thieno[2,3-c]pyridine-3- | 20 | P.O. | 349 ± 46** |

TABLE 55-continued

Anxiolytic effect

| Compound | Dose (mg/kg) | Administration route | Number of shock suffered (Number per 5 minutes) |
|---|---|---|---|
| carboxamide hydrochloride N-(2-pentyl)-1,2,3,4-tetrahydro-benzo[b]thieno[2,3-c]pyridine-3-carboxamide hydrochloride | 20 | P.O. | 351 ± 29** |

**$P < 0.05$ (t calibration).

TABLE 56

Anxiolytic effect

| Compound | Dose (mg/kg) | Administration route | Number of shock suffered (Number per 5 minutes) |
|---|---|---|---|
| N-(tert-amyl)-1,2,3,4-tetrahydro-benzo[b]thieno[2,3-c]pyridine-3-carboxamide hydrochloride | 20 | P.O. | 334 ± 32** |
| N-(1,2-dimethylpropyl)-1,2,3,4-tetrahydrobenzo[b]thieno[2,3-c]-pyridine-3-carboxamide hydrochloride | 20 | P.O. | 352 ± 36** |
| N-(1,5-dimethylhexyl)-1,2,3,4-tetrahydrobenzo[b]thieno[2,3-c]-pyridine-3-carboxamide hydrochloride | 20 | P.O. | 349 ± 46** |
| N-(2-ethylhexyl)-1,2,3,4-tetra-hydrobenzo[b]thieno[2,3-c]-pyridine-3-carboxamide | 20 | P.O. | 351 ± 29** |
| N-(1,1,3,3-tetramethylbutyl)-1,2,3,4-tetrahydrobenzo[b]thieno-[2,3-c]pyridine-3-carboxamide hydrochloride | 20 | P.O. | 334 ± 32** |

**$P < 0.05$ (t calibration).

TABLE 57

Anxiolytic effect

| Compound | Dose (mg/kg) | Administration route | Number of shock suffered (Number per 5 minutes) |
|---|---|---|---|
| N-ocyl-1,2,3,4-tetrahydrobenzo-[b]thieno[2,3-c]pyridine-3-carboxamide hydrochloride | 20 | P.O. | 352 ± 36** |
| N[(S)-(−)-2-methylbutyl]-1,2,3,4-tetrahydrobenzo[b]thieno[2,3-c]pyridine-3-carboxamide hydrochloride | 20 | P.O. | 349 ± 46** |
| N-(3,3-dimethylpropyl)-1,2,3,4-tetrahydrobenzo[b]thieno[2,3-c]-pyridine-3-carboxamide hydrochloride | 20 | P.O. | 351 ± 29** |
| cyclohexyl 1,2,3,4-tetrahydro-benzo[b]thieno[2,3-c]pyridine-3-carboxylate hydrochloride | 20 | P.O. | 334 ± 32** |
| cyclopenyl 1,2,3,4-tetrahydro-benzo[b]thieno[2,3-c]pyridine-3-carboxylate hydrochloride | 20 | P.O. | 352 ± 36** |

**$P < 0.05$ (t calibration).

TABLE 58

Anxiolytic effect

| Compound | Dose (mg/kg) | Administration route | Number of shock suffered (Number per 5 minutes) |
|---|---|---|---|
| cycloheptyl 1,2,3,4-tetrahydro-benzo[b]thieno[2,3-c]pyridine-3-carboxylate hydrochloride | 20 | P.O. | 378 ± 38** |
| cyclooctyl 1,2,3,4-tetrahydro-benzo[b]thieno[2,3-c]pyridine-3-carboxylate hydrochloride | 20 | P.O. | 375 ± 45** |
| cyclohexylmethyl 1,2,3,4-tetra-hydrobenzo[b]thieno[2,3-c]-pyridine-3-carboxylate hydrochloride | 20 | P.O. | 379 ± 35** |
| N-cyclohexyl-6-hydroxy-1,2,3,4-tetrahydrobenzo[b]thieno[2,3-c]-pyridine-3-carboxamide hydrochloride | 20 | P.O. | 336 ± 45** |
| N-cyclohexyl-1,2,3,4-tetrahydro-benzo[b]thieno[2,3-c]pyridine-3-carboxamide-9-oxide hydrochloride | 20 | P.O. | 358 ± 53** |

**$P < 0.05$ (t calibration).

TABLE 59

Anxiolytic effect

| Compound | Dose (mg/kg) | Administration route | Number of shock suffered (Number per 5 minutes) |
|---|---|---|---|
| N-cyclohexyl-6-hydroxy-1,2,3,4-tetrahydrobenzo[b]thieno[2,3-c]-pyridine-3-carboxamide-9-oxide hydrochloride | 20 | P.O. | 338 ± 46** |
| N-(4-hydroxycyclohexyl)-6-hydroxy-1,2,3,4-tetrahydrobenzo-[b]thieno[2,3-c]pyridine-3-carboxamide-9-oxide hydrochloride | 20 | P.O. | 347 ± 45** |
| N-cyclohexyl-1,2,3,4-tetrahydro-benzo[b]thieno[2,3-c]pyridine-3-carboxamide-9-dioxide hydrochloride | 20 | P.O. | 345 ± 39** |

**$P < 0.05$ (t calibration).

(Learning-improvement Effect)

Mice were used in this test. When mice were introduced into the light room of a light/dark box of step-through type, they moved into the dark room within several seconds. In the dark room, electric shock was applied to the animals (acquired trial). On the next day, the mice were introduced into the light room again. Then the memory of the electric shock on the previous day made these animals to hesitate to enter the dark room (regenerative trial). The period of time required for entering from the light room into the dark room on the next day (latent time) was employed as an indication of the learning memory. A longer latent time means the more improved learning/remembering ability. Each drug was administered before the acquired trial on the day 1.

Tables 60 to 76 show the data calculated by referring the average of control mice (no drug administration) as to 100 (n=8).

These results indicate that the compounds of the present invention significantly prolong the latent time and thus show a learning improvement effect, which suggest that these compounds are usable as an anxiolytic drug or a nootropic drug.

TABLE 60

Learning improvement effect

| Compound | Dose (mg/kg) | Administration route | Number of shock suffered (Number per 5 minutes) |
|---|---|---|---|
| Control | | | 100 ± 16.9 |
| N-(trans-4-hydroxycyclohexyl)-1,2,3,4-tetrahydrobenzo[b]-thieno[2,3-c]pyridine-3-carboxamide hydrochloride | 20 | P.O. | 332 ± 23** |

TABLE 60-continued

| | Learning improvement effect | | |
|---|---|---|---|
| Compound | Dose (mg/kg) | Administration route | Number of shock suffered (Number per 5 minutes) |
| N-(cis-4-hydroxycyclohexyl)-1,2,3,4-tetrahydrobenzo[b]-thieno[2,3-c]pyridine-3-carboxamide hydrochloride | 20 | P.O. | 326 ± 43** |
| (+)-N-(trans-4-hydroxycyclo-hexyl)-1,2,3,4-tetrahydrobenzo-[b]thieno[2,3-c]pyridine-3-carboxamide hydrochloride | 20 | P.O. | 388 ± 34** |
| (+)-N-(cis-4-hydroxycyclohexyl)-1,2,3,4-tetxahydrobenzo-[b]thieno[2,3-c]pyridine-3-carboxamide hydrochloride | 20 | P.O. | 338 ± 45** |

**$P < 0.05$ (t calibration).

TABLE 61

| | Learning improvement effect | | |
|---|---|---|---|
| Compound | Dose (mg/kg) | Administration route | Number of shock suffered (Number per 5 minutes) |
| (−)-N-(trans-4-hydroxycyclohexyl)-1,2,3,4-tetrahydrobenzo[b]thieno-[2,3-c]pyridine-3-carboxamide hydrochloride | 20 | P.O. | 347 ± 45** |
| (−)-N-(cis-4-hydroxycyclohexyl)-1,2,3,4-tetrahydrobenzo[b]-thieno[2,3-c]pyridine-3-carboxamide hydrochloride | 20 | P.O. | 346 ± 31** |
| N-(2-hydroxycyclohexyl)-1,2,3,4-tetrahydrobenzo[b]thieno[2,3-c]-pyridine-3-carboxamide hydrochloride | 20 | P.O. | 389 ± 42** |
| N-(4-methylcyclohexyl)-1,2,3,4-tetrahydrobenzo[b]thieno[2,3-c]-pyridine-3-carboxamide hydrochloride | 20 | P.O. | 355 ± 39** |
| N-(2-methylcyclohexyl)-1,2,3,4-tetrahydrobenzo[b]thieno[2,3-c]-pyridine-3-carboxamide hydrochloride | 20 | P.O. | 347 ± 35** |

**$P < 0.05$ (t calibration).

TABLE 62

| | Learning improvement effect | | |
|---|---|---|---|
| Compound | Dose (mg/kg) | Administration route | Number of shock suffered (Number per 5 minutes) |
| N-(4-tert-butylcyclohexyl)-1,2,3,4-tetrahydrobenzo[b]thieno[2,3-c]-pyridine-3-carboxamide | 20 | P.O. | 386 ± 49** |
| N-(4-aminocyclohexyl)-1,2,3,4-tetrahydrobenzo[b]thieno[2,3-c]-pyridine-3-carboxamide trihydrochloride | 20 | P.O. | 345 ± 50** |
| N-piperidino-1,2,3,4-tetrahydro-benzo[b]thieno[2,3-c]pyridine-3-carboxamide dihydrochloride | 20 | P.O. | 356 ± 45** |
| N-{1-(4-methylpiperazinyl)}-1,2,3,4-tetrahydrobenzo[b]thieno[2,3-c]pyridine-3-carboxamide trihydrochloride | 20 | P.O. | 344 ± 41** |
| N-(2,6-dimethylpyridino)-1,2,3,4-tetrahydrobenzo[b]thieno[2,3-c]- | 20 | P.O. | 335 ± 23** |

TABLE 62-continued

Learning improvement effect

| Compound | Dose (mg/kg) | Administration route | Number of shock suffered (Number per 5 minutes) |
|---|---|---|---|
| pyridine-3-carboxamide dihydrochloride | | | |

**$P < 0.05$ (t calibration).

TABLE 63

Learning improvement effect

| Compound | Dose (mg/kg) | Administration route | Number of shock suffered (Number per 5 minutes) |
|---|---|---|---|
| N-(1-pyrrolidinyl)-1,2,3,4-tetra-hydrobenzo[b]thieno[2,3-c]-pyridine-carboxamide hydrochloride | 20 | P.O. | 326 ± 54** |
| N-[1-{4-(2-hydroxyethyl)-piperazinyl}]-1,2,3,4-tetrahydro-benzo[b]thieno[2,3-c]pyridine-3-carboxamide trihydrochloride | 20 | P.O. | 388 ± 49** |
| N-{4-(1,2-diethylpyrrazolidinyl)}-1,2,3,4-tetrahydrobenzo[b]thieno-[2,3-c]pyridine-3-carboxamide trihydrochloride | 20 | P.O. | 339 ± 45** |
| N-cyclohexyl-N-methyl-1,2,3,4-tetrahydrobenzo[b]thieno[2,3-c]-pyridine-3-carboxamide hydrochloride | 20 | P.O. | 339 ± 42** |
| N-(4-pyridyl)-1,2,3,4-tetrahydro-benzo[b]thieno[2,3-c]pyridine-3-carboxanide hydrochloride | 20 | P.O. | 329 ± 42** |

**$P < 0.05$ (t calibration).

TABLE 64

Learning improvement effect

| Compound | Dose (mg/kg) | Administration route | Number of shock suffered (Number per 5 minutes) |
|---|---|---|---|
| N-phenyl-1,2,3,4-tetrahydro-benzo[b]thieno[2,3-c]pyridine-3-carboxamide hydrochloride | 20 | P.O. | 364 ± 35** |
| N-(1-pyrrolinyl)-1,2,3,4-tetra-hydrobenzo[b]thieno[2,3-c]-pyridine-3-carboxamide | 20 | P.O. | 361 ± 45** |
| N-{4-(1,2,4-triazolyl)}-1,2,3,4-tetrahydronzo[b]thieno[2,3-c]-pyridine-3-carboxamide hydrochloride | 20 | P.O. | 339 ± 43** |
| N-cyclooctyl-1,2,3,4-tetrahydro-benzo[b]thieno[2,3-c]pyridine-3-carboxamide hydrochloride | 20 | P.O. | 329 ± 23** |
| N-(4-piperidinyl)methyl-1,2,3,4-tetrahydrobenzo[b]thieno[2,3-c]-pyridine-3-carboxamide dihydrochloride | 20 | P.O. | 354 ± 50** |

**$P < 0.05$ (t calibration).

TABLE 65

Learning improvement effect

| Compound | Dose (mg/kg) | Administration route | Number of shock suffered (Number per 5 minutes) |
|---|---|---|---|
| N-cyclohexylmethyl-1,2,3,4-tetra-hydrobenzo[b]thieno[2,3-c]-pyridine-3-carboxamide hydrochloride | 20 | P.O. | 357 ± 45** |
| N-(3-pentyl)-1,2,3,4-tetrahydro-benzo[b]thieno[2,3-c]pyridine-3-carboxamide hydrochloride | 20 | P.O. | 363 ± 43** |
| N-diethyl-1,2,3,4-tetrahydro-benzo[b]thieno[2,3-c]pyrdine-3-carboxamide hydrochloride | 20 | P.O. | 321 ± 33** |
| N-(1-adamantyl)-1,2,3,4-tetra-hydrobenzo[b]thieno[2,3-c]-pyridine-3-carboximade hydrochloride | 20 | P.O. | 364 ± 35** |
| N-(3-quinuclidinyl)-1,2,3,4-tetrahydrobenzo[b]thieno[2,3-c]-pyridine-3-carboxamide dihydrochloride | 20 | P.O. | 387 ± 49** |

**P < 0.05 (t calibration).

TABLE 66

Learning improvement effect

| Compound | Dose (mg/kg) | Administration route | Number of shock suffered (Number per 5 minutes) |
|---|---|---|---|
| N-(exo-2-norbonyl)-1,2,3,4-tetra-hydrobenzo[b]thieno[2,3-c]-pyridine-3-carboxamide hydrochloride | 20 | P.O. | 373 ± 33** |
| N-(3-chlorophenyl)-4-{3-(1,2,3,4-tetrahydrobenzo[b]thieno[2,3-c]-pyridine)carbonyl}piperazine dihydrochloride | 20 | P.O. | 387 ± 43** |
| N-piperonyl-1,2,3,4-tetrahydro-benzo[b]thieno[2,3-c]pyridine-3-carboxamide hydrochloride | 20 | P.O. | 384 ± 45** |
| N-(2-methoxybenzyl)-1,2,3,4-tetrahydrobenzo[b]thieno[2,3-c]-pyridine-3-carboxamide hydrochloride | 20 | P.O. | 346 ± 33** |
| N-(3-methoxybenzyl)-1,2,3,4-tetrahydrobenzo[b]thieno[2,3-c]-pyridine-3-carboxamide hydrochloride | 20 | P.O. | 365 ± 35** |

**P < 0.05 (t calibration).

TABLE 67

Learning improvement effect

| Compound | Dose (mg/kg) | Administration route | Number of shock suffered (Number per 5 minutes) |
|---|---|---|---|
| N-(4-methoxybenzyl)-1,2,3,4-tetrahydrobenzo[b]thieno[2,3-c]-pyridine-3-carboxamide hydrochloride | 20 | P.O. | 362 ± 46** |
| N-(2,3-dimethoxybenzyl)-1,2,3,4-tetrahydrobenzo[b]thieno[2,3-c]-pyridine-3-carboxamide hydrochloride | 20 | P.O. | 389 ± 46** |
| N-{2,4-dimethoxybenzyl)-1,2,3,4-tetrahydrobenzo[b]thieno[2,3-c]-pyridine-3-carboxamide hydrochloride | 20 | P.O. | 358 ± 39** |
| N-(3,4-dimethoxybenzyl)-1,2,3,4- | 20 | P.O. | 364 ± 35** |

TABLE 67-continued

| | Learning improvement effect | | |
|---|---|---|---|
| Compound | Dose (mg/kg) | Administration route | Number of shock suffered (Number per 5 minutes) |
| tetrahydrobenzo[b]thieno[2,3-c]pyridine-3-carboxamide hydrochloride | | | |
| N-(3,5-dimethoxybenzyl)-1,2,3,4-tetrahydrobenzo[b]thieno[2,3-c]-pyridine-3-carboxamide hydrochloride | 20 | P.O. | 367 ± 48** |

**$P < 0.05$ (t calibration).

TABLE 68

| | Learning improvement effect | | |
|---|---|---|---|
| Compound | Dose (mg/kg) | Administration route | Number of shock suffered (Number per 5 minutes) |
| N-(2,4,6-trimethoxybenzyl)-1,2,3,4-tetrahydrobenzo[b]thieno[2,3-c]-pyridine-3-carboxamide hydrochloride | 20 | P.O. | 378 ± 44** |
| N-(3,4,5-trimethoxybenzyl)-1,2,3,4-tetrahydrobenzo[b]thieno[2,3-c]pyridine-3-carboxamide hydrochloride | 20 | P.O. | 367 ± 38** |
| N-(α-methylbenzyl)-1,2,3,4-tetrahydrobenzo[b]thieno[2,3-c]-pyridine-3-carboxamide hydrochloride | 20 | P.O. | 357 ± 35** |
| N-(4-methylbenzyl)-1,2,3,4-tetrahydrobenzo[b]thieno[2,3-c]-pyridine-3-carboxamide hydrochloride | 20 | P.O. | 363 ± 33** |
| N-[4-(trifluoromethyl)benzyl]-1,2,3,4-tetrahydrobenzo[b]thieno-[2,3-c]pyridine-3-carboxamide hydrochloride | 20 | P.O. | 363 ± 43** |

**$P < 0.05$ (t calibration).

TABLE 69

| | Learning improvement effect | | |
|---|---|---|---|
| Compound | Dose (mg/kg) | Administration route | Number of shock suffered (Number per 5 minutes) |
| N-[4-(isopropyl)benzyl]-1,2,3,4-tetrahydrobenzo[b]thieno[2,3-c]-pyridine-3-carboxamide hydrochloride | 20 | P.O. | 384 ± 35** |
| N-[4-(tert-butyl)benzyl]-1,2,3,4-tetrahydrobenzo[b]thieno[2,3-c]-pyridine-3-carboxamide hydrochloride | 20 | P.O. | 367 ± 42** |
| N-[4-(isopropyl)phenyl]-1,2,3,4-tetrahydrobenzo[b]thieno[2,3-c]-pyridine-3-carboxamide hydrochloride | 20 | P.O. | 354 ± 43** |
| N-[4-(tert-butyl)phenyl]-1,2,3,4-tetrahydrobenzo[b]thieno[2,3-c]-pyridine-3-carboxamide hydrochloride | 20 | P.O. | 377 ± 39** |
| N-[trans-2-(phenylcyclopropyl)]-1,2,3,4-tetrahydrobenzo[b]-thieno[2,3-c]pyridine-3-carboxamide hydrochloride | 20 | P.O. | 384 ± 35** |

**$P < 0.05$ (t calibration).

TABLE 70

Learning improvement effect

| Compound | Dose (mg/kg) | Administration route | Number of shock suffered (Number per 5 minutes) |
|---|---|---|---|
| N-ethynylcyclohexyl-1,2,3,4-tetrahydrobenzo[b]thieno[2,3-c]-pyridine-3-carboxamide hydrochloride | 20 | P.O. | 367 ± 46** |
| N-cyclononyl-1,2,3,4-tetrahydro-benzo[b]thieno[2,3-c]pyridine-3-carboxamide hydrochloride | 20 | P.O. | 387 ± 44** |
| N-cyclodecanyl-1,2,3,4-tetrahydro-benzo[b]thieno[2,3-c]pyridine-3-carboxamide hydrochloride | 20 | P.O. | 381 ± 38** |
| N-(2,3-dimethylcyclohexyl)-1,2,3,4-tetrahydrobenzo[b]thieno[2,3-c]pyridine-3-carboxamide hydrochloride | 20 | P.O. | 369 ± 47** |
| N-(tert-butyl)-1,2,3,4-tetrahydro-benzo[b]thieno[2,3-c]pyridine-3-carboxamide hydrochloride | 20 | P.O. | 377 ± 49** |

**$P < 0.05$ (t calibration).

TABLE 71

Learning improvement effect

| Compound | Dose (mg/kg) | Administration route | Number of shock suffered (Number per 5 minutes) |
|---|---|---|---|
| N-(isoamyl)-1,2,3,4-tetrahydro-benzo[b]thieno[2,3-c]pyridine-3-carboxamide hydrochloride | 20 | P.O. | 369 ± 41** |
| N-[(−)cis-myrtanyl]-1,2,3,4-tetrahydrobenzo[b]thieno[2,3-c]-pyridine-3-carboxamide hydrochloride | 20 | P.O. | 390 ± 47** |
| N-(endo-2-norbonyl)-1,2,3,4-tetrahydrobenzo[b]thieno[2,3-c]-pyridine-3-carboxamide hydrochloride | 20 | P.O. | 384 ± 46** |
| N-cyclododecyl-1 2,3,4-tetrahydro-benzo[b]thieno[2,3-c]pyridine-3-carboxamide hydrochloride | 20 | P.O. | 367 ± 45** |
| N-(isobutyl)-1,2,3,4-tetrahydro-benzo[b]thieno[2,3-c]pyridine-3-carboxamide hydrochloride | 20 | P.O. | 334 ± 32** |

**$P < 0.05$ (t calibration).

TABLE 72

Learning improvement effect

| Compound | Dose (mg/kg) | Administration route | Number of shock suffered (Number per 5 minutes) |
|---|---|---|---|
| N-diisopropyl-1,2,3,4-tetrahydro-benzo[b]thieno[2,3-c]pyridine-3-carboxamide hydrochloride | 20 | P.O. | 352 ± 36** |
| N-(1,3-dimethylbutyl)-1,2,3,4-tetrahydrobenzo[b]thieno[2,3-c]-pyridine-3-carboxamide hydrochloride | 20 | P.O. | 345 ± 39** |
| N-(2-heptyl)-1,2,3,4-tetrahydro-benzo[b]thieno[2,3-c]pyridine-3-carboxamide hydrochloride | 20 | P.O. | 329 ± 35** |
| N-(4-heptyl)-1,2,3,4-tetrahydro-benzo[b]thieno[2,3-c]pyridine-3-carboxamide hydrochloride | 20 | P.O. | 356 ± 49** |
| N-(2-octyl)-1,2,3,4-tetrahydro- | 20 | P.O. | 345 ± 54** |

TABLE 72-continued

| | Learning improvement effect | | |
|---|---|---|---|
| Compound | Dose (mg/kg) | Administration route | Number of shock suffered (Number per 5 minutes) |
| benzo[b]thieno[2,3-c]pyridine-3-carboxamide hydrochloride | | | |

**$P < 0.05$ (t calibration).

TABLE 73

| | Learning improvement effect | | |
|---|---|---|---|
| Compound | Dose (mg/kg) | Administration route | Number of shock suffered (Number per 5 minutes) |
| N-(sec-butyl)-1,2,3,4-tetrahydrobenzo[b]thieno[2,3-c]pyridine-3-carboxamide hydrochloride | 20 | P.O. | 349 ± 46** |
| N-(2-pentyl)-1,2,3,4-tetrahydrobenzo[b]thieno[2,3-c]pyridine-3-carboxamide hydrochloride | 20 | P.O. | 351 ± 29** |
| N-(tert-amyl)-1,2,3,4-tetrahydrobenzo[b]thieno[2,3-c]pyridine-3-carboxamide hydrochloride | 20 | P.O. | 334 ± 32** |
| N-(1,2-dimethylpropyl)-1,2,3,4-tetrahydrobenzo[b]thieno[2,3-c]-pyridine-3-carboxamide hydrochloride | 20 | P.O. | 352 ± 36** |
| N-(1,5-dimethylhexyl)-1,2,3,4-tetrahydrobenzo[b]thieno[2,3-c]pyridine-3-carboxamide hydrochloride | 20 | P.O. | 349 ± 46** |

**$P < 0.05$ (t calibration).

TABLE 74

| | Learning improvement effect | | |
|---|---|---|---|
| Compound | Dose (mg/kg) | Administration route | Number of shock suffered (Number per 5 minutes) |
| N-(2-ethylhexyl)-1,2,3,4-tetrahydrobenzo[b]thieno[2,3-c]-pyridine-3-carboxamide hydrochloride | 20 | P.O. | 351 ± 29** |
| N-(1,1,3,3-tetramethylbutyl)-1,2,3,4-tetrahydrobenzo[b]thieno[2,3-c]pyridine-3-carboxamide hydrochloride | 20 | P.O. | 334 ± 32** |
| N-octyl-1,2,3,4-tetrahydrobenzo-[b]thieno[2,3-c]pyridine-3-carboxamide hydrochloride | 20 | P.O. | 352 ± 36** |
| N-[(S)-(−)-2-methylbutyl]-1,2,3,4-tetrahydrobenzo[b]thieno[2,3-c]-pyridine-3-carboxamide hydrochloride | 20 | P.O. | 349 ± 46** |
| N-(3,3-dimethylpropyl)-1,2,3,4-tetrahydrobenzo[b]thieno[2,3-c]-pyridine-3-carboxamide hydrochloride | 20 | P.O. | 351 ± 29** |

**$P < 0.05$ (t calibration).

TABLE 75

Learning improvement effect

| Compound | Dose (mg/kg) | Administration route | Number of shock suffered (Number per 5 minutes) |
|---|---|---|---|
| cyclohexyl 1,2,3,4-tetrahydro-benzo[b]thieno[2,3-c]pyridine-3-carboxylate hydrochloride | 20 | P.O. | 377 ± 47** |
| cyclopentyl 1,2,3,4-tetrahydro-benzo[b]thieno[2,3-c]pyridine-3-carboxylate hydrochloride | 20 | P.O. | 367 ± 43** |
| cycloheptyl 1,2,3,4-tetrahydro-benzo[b]thieno[2,3-c]pyridine-3-carboxylate hydrochloride | 20 | P.O. | 388 ± 39** |
| cyclooctyl 1,2,3,4-tetra-hydrobenzo[b]thieno[2,3-c]-pyridine-3-carboxylate hydrochloride | 20 | P.O. | 371 ± 49** |
| cyclohexylmethyl 1,2,3,4-tetra-hydrobenzo[b]thieno[2,3-c]-pyridine-3-carboxylate hydrochloride | 20 | P.O. | 376 ± 29** |

**$P < 0.05$ (t calibration).

TABLE 76

Learning improvement effect

| Compound | Dose (mg/kg) | Administration route | Number of suffered shock (Number per 5 minutes) |
|---|---|---|---|
| N-cyclohexyl-6-hydroxy-1,2,3,4-tetrahydrobenzo[b]thieno[2,3-c]pyridine-3-carboxamide hydrochloride | 20 | P.O. | 356 ± 35** |
| N-cyclohexyl-1,2,3,4-tetrahydro-benzo[b]thieno[2,3-c]pyridine-3-carboxamide-9-oxide hydrochloride | 20 | P.O. | 388 ± 50** |
| N-cyclohexyl-6-hydroxy-1,2,3,4 benzo[b]thieno[2,3-c]-pyridine-3-carboxamide-9-oxide hydrochloride | 20 | P.O. | 348 ± 47** |
| N-(4-hydroxycyclohexyl)-6-hydroxy-1,2,3,4-tetrahydrobenzo[b]thieno-[2,3-c]-pyridine-3-carboxamide-9-oxide hydrochloride | 20 | P.O. | 367 ± 49** |
| N-cyclohexyl-1,2,3,4-tetrahydro-benzo[b]thieno[2,3-c]pyridine-3-carboxamide-9-dioxide hydrochloride | 20 | P.O. | 365 ± 49** |

**$P < 0.05$ (t calibration).

[Utilities of the Invention]

I. Utility-1

As discussed in the item for (Anxiolytic effect), it is clear in Table 42 in comparison in the dose and the anxiolytic effect that the compounds of the present invention are significantly different in the t calibration from β-carboline-3-ethyl ester (referred to simply as β-CCE) which is a typical example of the compounds disclosed in JP-A-56-43283, 6-chloro-1,2,3,4-tetrahydrobenzothieno[2,3-c]pyridine (referred to simply as C-1) which is a typical example of the compounds disclosed in JP-B-50-2519, ethyl benzothieno[2,3-c]pyridine-3-carboxylate (referred to simply as A-1) which is a typical example of the compounds disclosed in JP-A-61-236779, ethyl 1,2,3,4-tetrahydrobenzothieno[2,3-c]pyridine-3-carboxylate (referred to simply as A-2) which is a typical example of the compounds disclosed in JP-A-63-096188, hexahydro-1-(benzothieno[2,3-c]pyridine-3-carbonyl)-1H-1,4-diazepine (referred to simply as A-3) which is a typical example of the compounds disclosed in JP-A-63-096189, N-(2-aminoethylbenzothieno[2,3-c]pyridine-3-carboxamide (referred to simply as A-4) which is a typical example of the compounds disclosed in JP-A-1-100172 and N-ethyl-1,2,3,4-tetrahydrobenzothieno[2,3-c]pyridine-3-carboxamide (referred to simply as A-5) which is a typical example of the compounds disclosed in JP-A-2-149583. A comparison of the compounds of the present invention with N-cyclohexyl-1,2,3,4-tetrahydrobenzothieno[2,3-c]pyridine-3-carboxamide hydrochloride (referred to simply as A-6) which is a typical example of the compounds disclosed in JP-A-2-149583 indicates that A-6 exhibited the effect at a dose of 30 mg/kg while the compounds of the present invention exhibited the effect of 20 mg/kg, i.e., ⅔ times as much as A-6. That is to say, the compound of the present invention is a significant useful over publicly known ones.

II. Utility-2

(Light/dark Exploratory Test)
(Experimental Method)

This test was performed by using male ddy mice aged 6 weeks in accordance with Crawley J. and Goodwin F. K., Pharmacol. Biochem. Behav., 13, 167–170 (1980).

A group to which physiological saline was given had 10 animals while other groups had each 20 animals. Physiological saline or each test compound was orally administered to mice. An hour later, the animals were introduced into a light/dark exploratory device made of an acrylic resin (light room: 20×20×10 cm, dark room: 10×20×10 cm). After observing for 10 minutes, the resident time of each mouse in the light room was measured. Table 77 shows the results.

TABLE 77

| Group | No. of mice | Dose (mg/kg) | Resident time in light room (sec.) |
|---|---|---|---|
| Control | 10 | — | 73.2 ± 6.2 |
| A-7 | 20 | 3 | 121.4 ± 14.9 |
|  | 20 | 10 | 141.3 ± 18.4 |
|  | 20 | 30 | 191.1 ± 23.1 |
| A-6 | 20 | 3 | 79.2 ± 11.1 |
|  | 20 | 10 | 98.4 ± 20.2 |
|  | 20 | 30 | 152.4 ± 15.2 |

RESULTS AND DISCUSSION

The administration of N-cyclohexyl-1,2,3,4-tetrahydrobenzothieno[2,3-c]pyridine-3-carboxamide hydrochloride (referred to simply as A-6) disclosed in JP-A-2-149583 prolonged the resident time in the light room depending on the dose and a significant effect was observed at a dose of 30 mg/kg. On the other hand, the administration of N-piperonyl-1,2,3,4-tetrahydrobenzo[b]thieno[2,3-c]pyridine-3-carboxamide hydroxide (referred to simply as A-7), i.e., the compound of the present invention also prolonged the resident time in the light room depending on the dose, as shown in Table 77. Compared with A-6, A-7 showed this effect at a lower dose and a significant effect was observed at 3 mg/kg. The prolongation effect of A-7 at 3 mg/kg was significantly higher than that of A-6 at 3 mg/kg.

In this exploratory test, a device consisting of two compartments, i.e., a light room and a dark room was used. It was obvious that the dark room is preferable for mice. It appears that these animals are unfamiliar with the light room which is made of a transparent acrylic resin and under illumination with a fluorescent lamp. Therefore, it is considered clear that the mice have a stress for staying in the light room, whereby they become anxious. In fact, it is reported that the administration of a drug having an anxiolytic effect can prolong the resident time in the light room (M. Carli, C. Prontera and R. Samanin, Br. J. Pharmacol., 96, 829–836 (1986); and B. Costall, A. M. Domeney, P. A. Gerard, M. E. Kelly, R. J. Naylor, J. Pharm. Pharmacol., 40, 302–305 (1988)). Accordingly, it is considered that A-6 and A-7 both exerted an anxiolytic effect and thus prolonged the resident time in the light room. Compared with A-6 the anxiolytic effect of which has been reported, A-7 showed a significantly stronger effect. Thus it is suggested that the anxiolytic effect of A-7 is significantly higher than that of A-6.

A conflict test method has been widely known as a method whereby anxiolytic effect is evaluated on a preclinical level. In this method, a skinner box is used and an experimental conflict state with a combination of award (feed and water) with penalty (electric shock) is formed. This system is suitable for evaluating benzodiazepine drugs and has been widely applied. However, it is known that recent anxiolytic drugs acting on various serotonin receptors would not always show strong anti-conflict effect in this system. In fact, it is considered that this system causes not anxiety but rather a stress, i.e., a reflection of a fear of directly suffering from the electric shock. In recent years, therefore, attempts have been made to establish a more natural method for evaluating anxiety accompanied by no physical stimulation. The brightness exploratory method employed in this test, wherein the nature of mice of preferring a dark place to a new light place is utilized, is characterized by causing no physical stimulation. It is known that not only benzodiazepine drugs but also anxiolytic drugs acting on serotonin receptors can be similarly evaluated by this system. Prolongation of the resident time in the light compartment is seemingly the result of overcoming anxiety for the light environment. Although A-7 showed an anxiolytic effect comparable to that of A-6 in the conflict system, the former effect was clearly higher than the latter in this light/dark exploratory system. That is to say, it is suggested that A-7, which is a typical example of the compound of the present invention, is significantly superior to A-6, which is a typical example of the compounds of JP-A-2-149583, in the anxiolytic effect under a stress-free environment.

It is described in Table 42 that A-7, which is a typical example of the compound of the present invention, is superior to those reported in conventional references in the anxiolytic effect.

INDUSTRIAL APPLICABILITY

When administered to man or animals in a free from or a salt form, the compound of the present invention exhibits strong anxiolytic and learning-improvement effects. Also, it has a low toxicity. These characteristics make it highly suitable as an anxiolytic drug and a drug for learning improvement.

It is claimed:

1. A tetrahydropyridine derivative represented by the following formula (1):

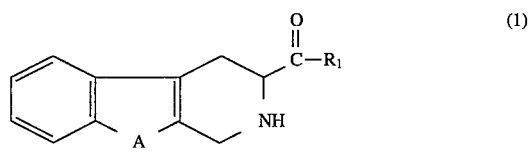

wherein A represents a sulfur atom, a sulfoxide group or a sulfone group; $R_1$ represents a piperonylamino group, a 2-methoxybenzylamino group, a 3-methoxybenzylamino group, a 4-methoxybenzylamino group, a 2,3-dimethoxybenzylamino group, a 2,4-dimethoxybenzylamino group, a 3,4-dimethoxybenzylamino group, a 3,5-dimethoxybenzylamino group, a 2,4,6-trimethoxybenzylamino group, a 3,4,5-trimethoxybenzylamino group, an α-methylbenzylamino group, a 4-methylbenzylamino group, a 4-(trifluoromethyl)benzylamino group, a 4-(isopropyl)benzylamino group, or a 4-(tert-butyl)benzylamino group, or a pharmaceutically acceptable acid addition salt thereof.

2. The tetrahydropyridine derivative of claim 1, which is N-piperonyl-1,2,3,4-tetrahydrobenzo[b]thieno[2,3-c]pyridine-3-carboxamide or a pharmaceutically acceptable acid addition salt thereof.

* * * * *